United States Patent
Ahn et al.

(10) Patent No.: US 10,236,081 B2
(45) Date of Patent: Mar. 19, 2019

(54) DEVICE FOR PROVIDING HEALTH MANAGEMENT SERVICE AND METHOD THEREOF

(71) Applicant: SAMSUNG ELECTRONICS CO., LTD., Suwon-si, Gyeonggi-do (KR)

(72) Inventors: Hyun Gi Ahn, Seoul (KR); Dong Hyun Roh, Yongin-si (KR); Kyung Sub Min, Seongnam-si (KR)

(73) Assignee: SAMSUNG ELECTRONICS CO., LTD., Suwon-si, Gyeonggi-do (KR)

( * ) Notice: Subject to any disclaimer, the term of this patent is extended or adjusted under 35 U.S.C. 154(b) by 0 days.

(21) Appl. No.: 15/829,201

(22) Filed: Dec. 1, 2017

(65) Prior Publication Data

US 2018/0157801 A1 Jun. 7, 2018

(30) Foreign Application Priority Data

Dec. 1, 2016 (KR) .................. 10-2016-0163038

(51) Int. Cl.
*G08B 21/02* (2006.01)
*G16H 40/63* (2018.01)
(Continued)

(52) U.S. Cl.
CPC ......... *G16H 40/63* (2018.01); *G06F 19/3418* (2013.01); *G06Q 50/22* (2013.01);
(Continued)

(58) Field of Classification Search
CPC ............ A61N 1/37247; A61N 1/37282; A61N 1/3621; A61N 1/37217; A61N 1/37235;
(Continued)

(56) References Cited

U.S. PATENT DOCUMENTS 8,157,730 B2   4/2012   LeBoeuf et al.
8,204,786 B2   6/2012   LeBoeuf et al.
(Continued)

FOREIGN PATENT DOCUMENTS

EP      3 079 090      10/2016

OTHER PUBLICATIONS

Extended Search Report dated Mar. 1, 2018 in counterpart European Patent Application No. 17204319.2.

*Primary Examiner* — Daniel Previl
(74) *Attorney, Agent, or Firm* — Nixon & Vanderhye, P.C.

(57) ABSTRACT

An electronic device includes a display, communication circuitry, at least one sensor, and a processor electrically connected with the display and the at least one sensor. The processor is configured to, based on state information obtained by the at least one sensor satisfying a predefined condition when a health state of a user corresponds to a first state, control transmitting the state information to an external server through the communication circuitry, control receiving from the external server a symptom check result corresponding to the state information, set a health state of the user to a second state based on the symptom check result, and provide a user interface (UI) for user health management at least once until the health state of the user changes from the second state to the first state based on at least one of the state information and the symptom check result.

20 Claims, 12 Drawing Sheets

(51) Int. Cl.
  *G06Q 50/22* (2018.01)
  *G06F 19/00* (2018.01)
  *G16H 50/20* (2018.01)
  *G16H 40/67* (2018.01)
  *G16H 20/30* (2018.01)
(52) U.S. Cl.
  CPC ............. *G16H 20/30* (2018.01); *G16H 40/67* (2018.01); *G16H 50/20* (2018.01)
(58) Field of Classification Search
  CPC ............ A61N 1/37252; A61N 1/37258; A61N 1/37264; A61N 1/37288; A61N 1/3962; A61N 1/3727; A61N 1/3906; A61N 1/3956; G06F 19/341
  USPC ... 340/573.1, 539.12, 539.11, 539.1, 539.22, 340/539.24, 539.29, 575, 571, 340/572.1–572.9, 573.5, 586, 636.11, 340/691.6
  See application file for complete search history.

(56) References Cited

U.S. PATENT DOCUMENTS

| | | | |
|---|---|---|---|
| 8,702,607 | B2 | 4/2014 | LeBoeuf et al. |
| 9,704,209 | B2 | 7/2017 | Proud et al. |
| 2004/0249299 | A1* | 12/2004 | Cobb ................... A61B 5/0205 600/529 |
| 2008/0004510 | A1* | 1/2008 | Tanzawa .............. A44C 5/0015 600/301 |
| 2008/0146892 | A1* | 6/2008 | LeBoeuf ................. A61B 5/11 600/300 |
| 2011/0098112 | A1 | 4/2011 | LeBoeuf et al. |
| 2011/0106627 | A1 | 5/2011 | LeBoeuf et al. |
| 2012/0197737 | A1 | 8/2012 | LeBoeuf et al. |
| 2012/0203081 | A1 | 8/2012 | LeBoeuf et al. |
| 2012/0226111 | A1 | 9/2012 | LeBoeuf et al. |
| 2012/0226112 | A1 | 9/2012 | LeBoeuf et al. |
| 2014/0107932 | A1 | 4/2014 | Luna |
| 2014/0249853 | A1* | 9/2014 | Proud ................... G06Q 50/24 705/3 |
| 2014/0275855 | A1 | 9/2014 | LeBoeuf et al. |
| 2014/0287833 | A1 | 9/2014 | LeBoeuf et al. |
| 2014/0288396 | A1 | 9/2014 | LeBoeuf et al. |
| 2014/0335490 | A1 | 11/2014 | Baarman et al. |
| 2015/0141772 | A1 | 5/2015 | LeBoeuf et al. |
| 2015/0351651 | A1* | 12/2015 | Chen ................... A61B 5/04014 600/374 |
| 2016/0058394 | A1* | 3/2016 | Koyama ............... A61B 5/0002 340/573.1 |
| 2016/0162019 | A1* | 6/2016 | Kang ..................... G06F 3/011 345/156 |
| 2016/0287142 | A1* | 10/2016 | Han ...................... A61B 5/7405 |
| 2016/0317049 | A1 | 11/2016 | LeBoeuf et al. |
| 2017/0000356 | A1* | 1/2017 | Smith, Sr. .......... A61B 5/02055 |
| 2017/0011200 | A1* | 1/2017 | Arshad ................ G06F 19/3456 |

* cited by examiner

DEVICE FOR PROVIDING HEALTH MANAGEMENT SERVICE AND METHOD THEREOF

CROSS-REFERENCE TO RELATED APPLICATION

This application is based on and claims the benefit under 35 U.S.C. § 119 of Korean Patent Application No. 10-2016-0163038 filed on Dec. 1, 2016 in the Korean Intellectual Property Office, the disclosure of which is incorporated by reference herein in its entirety.

TECHNICAL FIELD

The present disclosure relates generally to an electronic device and a method capable of providing a health management service.

BACKGROUND AND SUMMARY

As functions of smartphones, wearable devices, and electronic devices mountable on a car or a bike diversify, services for recording and managing the health of a user are being provided. For example, an electronic device may collect a heart rate or the like through various sensors. Also, applications provided in the electronic device can provide a function of recording a heart rate or the like of the user.

In a health management application/service provided in a conventional electronic device, the user may directly execute an application to check his/her health. For example, in a case in which the electronic device records a heart rate of the user, the user may execute an application to verify whether his/her heart rate is abnormal.

In the case of the above-described existing health management application/service, to check whether his/her health is abnormal, the user may directly execute the application. Also, in a case in which the user's health is abnormal, because the user directly checks whether symptoms disappear, the existing application/service may fail to provide a health management service sufficiently.

Various non-limiting example embodiments of the present disclosure may check symptoms at a necessary time point, even though a user does not perceive the symptoms, may provide a recovery guide for treating the symptoms, and may provide a recovery guide associated with the symptoms until the health of the user returns to normal.

In accordance with an example aspect of the present disclosure, an electronic device may include a display, communication circuitry, at least one sensor, and a processor electrically connected with the display and the at least one sensor. The processor may be configured to, based on state information obtained by the at least one sensor satisfying a predefined condition when a health state of a user corresponds to a first state; control transmitting the state information to an external server through the communication unit; control receiving from the external server, through the communication circuitry, a symptom check result corresponding to the state information; set a health state of the user to a second state based on the symptom check result; and provide a user interface (UI) for user health management at least once until the health state of the user changes from the second state to the first state based on at least one of the state information and the symptom check result.

In accordance with another example aspect of the present disclosure, a method may include obtaining state information of a user; transmitting, based on the obtained state information satisfying a predefined condition when a health state of the user corresponds to a first state, the state information to an external server; receiving, from the external server, a symptom check result corresponding to the state information; setting a health state of the user to a second state based on the symptom check result; and providing a user interface (UI) for user health management at least once until the health state of the user changes from the second state to the first state based on at least one of the state information and the symptom check result.

In accordance with another example aspect of the present disclosure, a recording medium may include instructions that, when executed by an electronic device providing a function of managing health of a user, cause the electronic device to perform obtaining state information of a user; transmitting, based on the obtained state information satisfying a predefined condition when a health state of the user corresponds to a first state, the state information to an external server; receiving, from the external server, a symptom check result corresponding to the state information; setting a health state of the user to a second state based on the symptom check result; and providing a user interface (UI) for user health management at least once until the health state of the user changes from the second state to the first state based on at least one of the state information and the symptom check result.

According to example embodiments of the present disclosure, it may be possible to check symptoms at a point in time when there is a need to check symptoms and to provide a recovery guide for treating the symptoms.

Also, it may be possible to check symptoms of a user based on data for each user and to provide a recovery guide associated with symptoms until health of the user becomes normal.

In addition, a variety of effects directly or indirectly understood through this disclosure may be provided.

BRIEF DESCRIPTION OF THE DRAWINGS

The above and other aspects, features, and attendant advantages of the present disclosure will be more apparent and readily appreciated from the following detailed description taken in conjunction with the accompanying drawings, in which like reference numerals refer to like elements, and wherein.

DETAILED DESCRIPTION

Figure 1:
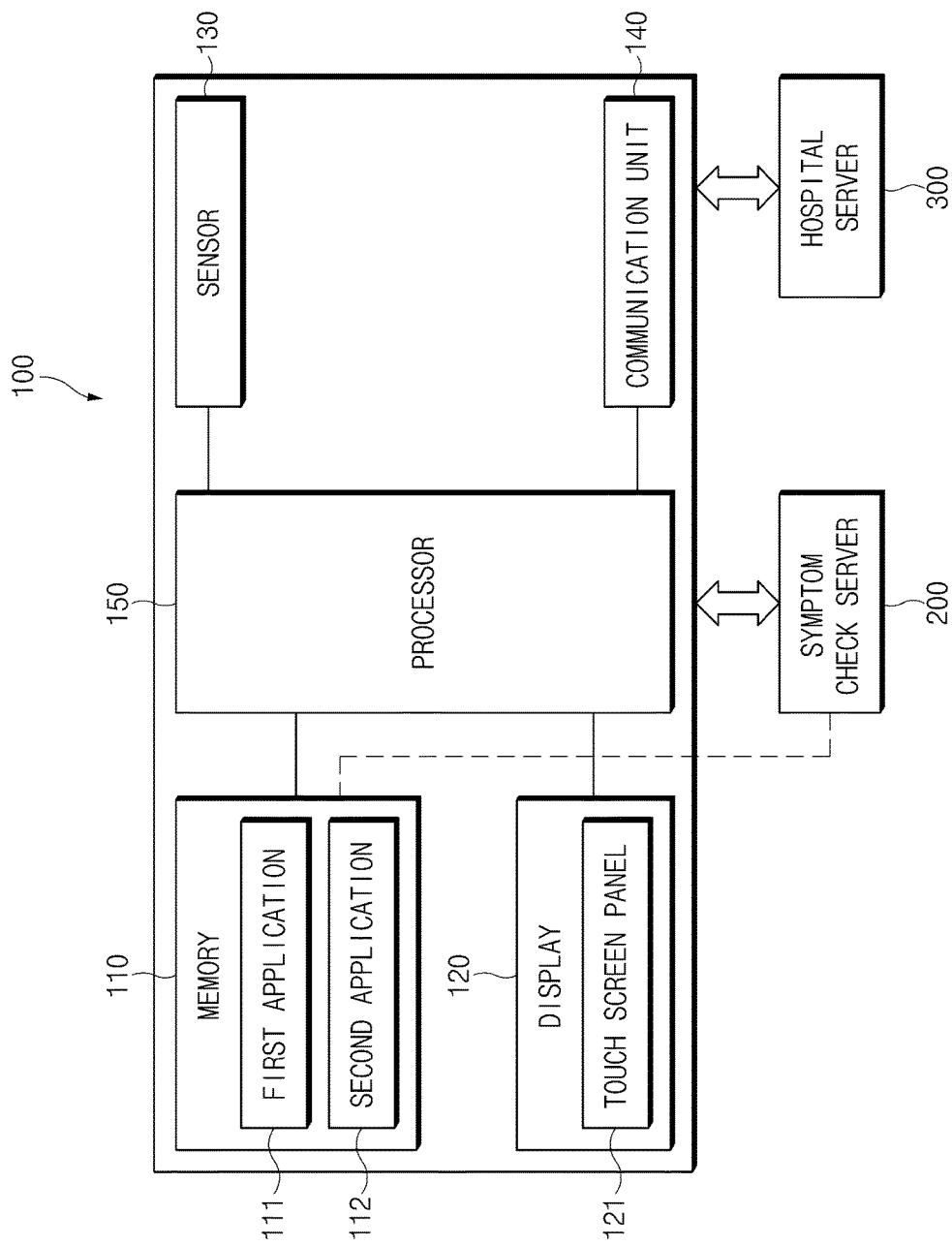
FIG. 1 is a block diagram illustrating an example electronic device providing a health management user interface (UI), a symptom check server, and a hospital server, according to various example embodiments of the present disclosure.

Hereinafter, various example embodiments of the present disclosure are described with reference to accompanying drawings. Accordingly, those of ordinary skill in the art will recognize that many modifications, equivalents, and/or alternatives of the example embodiments described herein can be variously made without departing from the scope and spirit of the present disclosure. With regard to description of drawings, similar elements may be marked by similar reference numerals.

The terms of a singular form may include plural forms unless otherwise specified. In this disclosure, the expressions "A or B", "at least one of A or/and B", or "one or more of A or/and B", and the like may include any and all combinations of one or more of the associated listed items. The terms, such as "first", "second", and the like may be used to refer to various elements regardless of the order and/or the priority and to distinguish the relevant elements from other elements, but do not limit the elements. When an element (e.g., a first element) is referred to as being "(operatively or communicatively) coupled with/to" or "connected to" another element (e.g., a second element), the element may be directly coupled with/to or connected to the other element or an intervening element (e.g., a third element) may be present.

According to the situation, the expression "configured to" used in this disclosure may be used interchangeably with, for example, the expression "suitable for", "having the capacity to", "adapted to", "made to", or "capable of", or "designed to" in hardware or software. The expression "a device configured to" may refer to a situation in which the device is "capable of" operating together with another device or other components. For example, a "processor configured to (or set to) perform A, B, and C" may refer, for example and without limitation, a dedicated processor (e.g., an embedded processor) for performing a corresponding operation or a generic-purpose processor (e.g., a central processing unit (CPU) or an application processor) which performs corresponding operations by executing one or more software programs which are stored in a memory device, or the like.

An electronic device according to various example embodiments of this disclosure may include at least one of, for example and without limitation, smartphones, tablet personal computers (PCs), mobile phones, video telephones, electronic book readers, desktop PCs, laptop PCs, netbook computers, workstations, servers, personal digital assistants (PDAs), portable multimedia players (PMPs), Motion Picture Experts Group (MPEG-1 or MPEG-2) Audio Layer 3 (MP3) players, medical devices, cameras, or wearable devices. According to various example embodiments, the wearable device may include, without limitation, at least one of an accessory type (e.g., watches, rings, bracelets, anklets, necklaces, glasses, contact lens, or head-mounted-devices (HMDs), a fabric or garment-integrated type (e.g., an electronic apparel), a body-attached type (e.g., a skin pad or tattoos), or a bio-implantable type (e.g., an implantable circuit). According to various example embodiments, the electronic device may include, without limitation, at least one of, for example, televisions (TVs), digital versatile disc (DVD) players, audios, refrigerators, air conditioners, cleaners, ovens, microwave ovens, washing machines, air cleaners, set-top boxes, home automation control panels, security control panels, media boxes (e.g., Samsung HomeSync™, Apple TV™, or Google TV™), game consoles (e.g., Xbox™ or PlayStation™), electronic dictionaries, electronic keys, camcorders, electronic picture frames, or the like.

According to another example embodiment, an electronic device may include at least one of various medical devices (e.g., various portable medical measurement devices (e.g., a blood glucose monitoring device, a heartbeat measuring device, a blood pressure measuring device, a body temperature measuring device, and the like), a magnetic resonance angiography (MRA), a magnetic resonance imaging (MRI), a computed tomography (CT), scanners, and ultrasonic devices), navigation devices, Global Navigation Satellite System (GNSS), event data recorders (EDRs), flight data recorders (FDRs), vehicle infotainment devices, electronic equipment for vessels (e.g., navigation systems and gyrocompasses), avionics, security devices, head units for vehicles, industrial or home robots, drones, automatic teller's machines (ATMs), points of sales (POSs) of stores, or internet of things (e.g., light bulbs, various sensors, sprinkler devices, fire alarms, thermostats, street lamps, toasters, exercise equipment, hot water tanks, heaters, boilers, and the like), or the like, but is not limited thereto. According to an example embodiment, the electronic device may include at least one of parts of furniture or buildings/structures, electronic boards, electronic signature receiving devices, projectors, or various measuring instruments (e.g., water meters, electricity meters, gas meters, or wave meters, and the like), or the like, but is not limited thereto. According to various example embodiments, the electronic device may be a flexible electronic device or a combination of two or more above-described devices. Furthermore, an electronic device according to an embodiment of this disclosure may not be limited to the above-described electronic devices. In this disclosure, the term "user" may refer to a person who uses an electronic device or may refer to a device (e.g., an artificial intelligence electronic device) that uses the electronic device.

FIG. 1 is a block diagram illustrating an electronic device providing a health management user interface (UI), a symptom check server, and a hospital server, according to various example embodiments of the present disclosure.

Referring to FIG. 1, an electronic device 100 may include a memory 110, a display 120, at least one sensor 130, a communication unit 140, a processor 150, and the like. However, the elements illustrated in FIG. 1 are not essential. For example, the electronic device 100 may be implemented to include additional elements or fewer elements.

The memory 110 may store a command or data associated with at least one other element of the electronic device 100. According to an example embodiment, the memory 110 may store a first application 111 for managing a health state of a user and a second application 112 for checking the health state of the user. The first application 111 may include a guide for health management of the user. The second application 112 may relate to a disease associated with symptoms and a recovery guide for the disease and may connect with a symptom check server 200 to receive information about a disease associated with symptoms and a recovery guide for the disease. The memory 110 may store schedule information of the user.

The display 120 may display (output) information processed in the electronic device 100. For example, the display 120 may display a user interface (UI) or a graphic user interface (GUI) associated with an operating mode of the electronic device 100.

The display 120 may include a touch screen panel 121. In a case in which the display 120 includes the touch screen panel 121, the display 120 may also be used as an input device. The touch screen panel 121 may have, for example, the form of a touch film, a touch sheet, a touch pad, or the like.

When a touch input to the touch screen panel 121 occurs, a signal corresponding to the touch input may be provided to a touch controller. The touch controller may process the provided signal and may transmit data corresponding to the processed result to the processor 150. As such, the processor 150 may recognize whether any area of the display 120 is touched.

The at least one sensor 130 may obtain state information of the user. For example, the at least one sensor 130 may include, without limitation, at least one of an electromyography (EMG) sensor, an electroencephalogram (EEG) sensor, an electrocardiogram (ECG) sensor, an oxygen saturation measurement sensor, a gesture sensor, a gyro sensor, a barometric pressure sensor, a magnetic sensor, an acceleration sensor, a grip sensor, a proximity sensor, a temperature/humidity sensor, a photoplethysmograph (PPG) sensor, and a gas sensor. The type of sensor 130 is not limited to these examples.

The state information that the sensor 130 obtains may include, without limitation, biometric information, movement information, and environment information. For example, the biometric information may include, without limitation, a heart rate, oxygen saturation in blood, blood sugar, blood pressure, a body temperature, EMG, ECG, EEG, and the like. The movement information may include, but is not limited to, a step pattern, a step count, a step time, a movement pattern, a movement time, a sleep pattern, a sleep time, and the like. The environment information may include, without limitation, the concentration of fine dust, the concentration of carbon monoxide, an ultraviolet (UV) index, a noise index, and the like. The state information that the sensor 130 obtains may be processed to new information by the sensor 130 or the processor 150. For example, the sensor 130 or the processor 150 may create step pattern information of the user based on values that the acceleration sensor and the gyro sensor measure, and the processor 150 may determine whether a step pattern satisfies a predefined condition, based on the created step pattern information.

The communication unit 140 may include communication circuitry for communicating with an external device or an external server. For example, the communication unit 140 may receive state information of the user from a wearable device. Also, as will be described below, the communication unit 140 may transmit the state information of the user and a user input to the symptom check server 200 or a hospital server 300 and may receive information about a disease or illness of the user. Additionally, the communication unit 140 may receive context information, such as day, date, weather, schedule information of the user, and environment information, from the external device or the external server.

The processor 150 (e.g., a CPU, ASIC, and/or other circuitry) may be electrically connected with the display 120 and the sensor 130 and may control overall operations of the electronic device 100.

If state information obtained by the at least one sensor 130 when the health state of the user corresponds to a first state satisfies a predefined condition, the processor 150 may transmit the state information of the user to the external server, such as the symptom check server 200 or the hospital server 300, through the communication unit 140.

The first state may be a state in which it is determined that the user's health is normal. The first state may be defined by the processor 150 based on the state information of the user. For example, the processor 150 may define a normal state of the user based on state information obtained by the at least one sensor 130 during a specified time period (e.g., over several hours, days, weeks, months, etc.). For example, in a case in which the processor 150 obtains the state information of the user, which indicates that a wake-up time of the user is 6 AM to 7 AM and a (resting) heart rate is 55 to 75 BPM, for two weeks, the processor 150 may determine that the health state of the user is normal when a wake-up time is between 6 AM to 7 AM and a heart rate is between 55 to 75 BPM, based on the obtained state information.

In the above example, the predefined condition may be satisfied in a case in which the obtained state information does not correspond to the defined normal state. For example, the predefined condition is satisfied in the case in which a wake-up time of the user included in the state information that the processor 150 obtains is 8 AM or a heart rate included therein is 90 BPM.

The predefined condition may be defined based on the context information obtained by the communication unit 140 and the user's state information. For example, in a case in which day information is obtained as context information by the communication unit 140 and the processor 150 obtains state information indicating that, for two weeks, a weekday wake-up time of the user is 6 AM to 7 AM and a weekend wake-up time is 9 AM to 10 AM, the processor 150 may determine that the health state of the user is normal when a weekday wake-up time is between 6 AM to 7 AM and a weekend wake-up time is between 9 AM to 10 AM.

The processor 150 may display a first UI on the display 120 before transmitting the state information to the external server through the communication unit 140. In a case in which the processor 150 obtains a user input through the first UI, the processor 150 may transmit the obtained user input to the external servers 200 and/or 300.

The first UI may include a health query UI, a UI to query whether to check symptoms, a symptom check UI, and the like.

For example, the health query UI may include state information of the user, a message to query whether the health state of the user corresponds to a normal state, and an object for receiving user input (e.g., a touch button).

The processor 150 may determine a health query UI to be displayed on the display 120 based on context information. The context information that the processor 150 depends on may be context information associated with the state information of the user. The context information may include schedule information of the user and environment information. For example, if a breathing pattern of the user is irregular, the processor 150 may determine a message to be included in the health query UI based on environment information associated with breathing such as the concentration of fine dust, the concentration of carbon monoxide, and the like.

In an example in which a message to be included in the health query UI is determined, it is assumed that, since the breathing pattern of the user is irregular, a breathing pattern being the state information satisfies a predefined condition. In a case in which the concentration of fine dust (the context information) is less than a specific value, the processor 150 may determine a message to be included in the health query UI as a message (e.g., "Your breathing is abnormal! Do you feel uncomfortable anywhere?") not associated with context information. In a case in which the concentration of fine dust is not less than the specific value, the processor 150 may determine a message to be included in the health query UI as a message (e.g., "Your breathing is different from usual. Fine dust is measured high. We recommend staying inside. Do you feel uncomfortable anywhere?") associated with context information.

In this example, the irregular breathing pattern of the user may be caused by the concentration of fine dust, not an abnormal health state of the user. Even though the breathing pattern (the state information) of the user is irregular and thus satisfies the predefined condition, the processor 150 may not display the health query UI including a query message associated with health and instead may display a message (e.g., "Your breathing is different from usual. Fine dust is measured high. We recommend staying inside.") including only information about the state information and the context information.

The processor 150 may display the UI to query whether to check symptoms. Also, the processor 150 may display the symptom check UI.

The UI to query whether to check symptoms may include a message to query whether to check symptoms, an object to receive a user input associated with querying whether to check symptoms (e.g., a touch button), and the like. For example, the message to query whether to check symptoms may be a message "Would you like to check your symptoms?".

In a case in which a user input to the UI to query whether to check symptoms is a response indicating that the user does not desire to check symptoms, the processor 150 may provide a guide for health management of the user. For example, the processor 150 may provide a health management guide message "Drinking plenty of water is good for your health".

The symptom check UI may include state information of the user, a message to check symptoms, an object to receive a user input associated with checking symptoms (e.g., a touch button), and the like. For example, the message to check symptoms may be a message "Do you have a headache?".

When displaying the symptom check UI, the processor 150 may control the display 120 to display a UI to query whether there are specific symptoms. The processor 150 may determine a type of symptoms that the symptom check UI queries, based on the state information of the user. For example, in a case in which a heart rate of the user is measured as being high, the processor 150 may display a UI including a message to query whether there is heart pain on the display 120. That is, the processor 150 may determine "heart pain" as being a type of symptom to be queried based on "heart rate" being the state information, and a UI to query whether there are symptoms may query whether there is heart pain. The UI to query whether there are symptoms may query whether there are mental symptoms, as well as whether there are physical symptoms.

Also, in a case in which a user's temperature is measured as being high, the processor 150 may display a UI to query "whether there are cold symptoms" or "whether there is abdominal pain" related to a "high fever".

The processor 150 may control display 120 to display a plurality of symptom check UIs for the purpose of determining a disease or illness of the user. Accordingly, the processor 150 may receive a plurality of user inputs associated with checking symptoms.

After displaying the symptom check UI to receive user input associated with checking symptoms, the processor 150 may display a UI to check any other symptoms. In this case, the processor 150 may determine a UI for checking any other symptoms to be displayed, based on the received user input. For example, in a case in which a message of the symptom check UI is "Do you have a headache?" and a user input associated with the message is "yes", the processor 150 may display a UI to check other symptoms associated with headache. For example, the processor 150 may display a UI including a message to check symptoms associated with headache, such as "Do you have migraine?", "Does the back of the head hurt?", or "Do you have a fever?".

The processor 150 may determine the symptom check UI based further on schedule information of the user, as well as the state information of the user. The schedule information that the processor 150 depends on may be schedule information associated with the state information of the user. For example, if a blood sugar value of the user is measured as being high, the processor 150 may determine the symptom check UI based on meal schedule information associated with the measured blood sugar value.

As an example to determine the symptom check UI, in a case in which a step pattern of the user obtained by the sensor 130 is different from a normal step pattern and a soccer schedule is included in the schedule information, the processor 150 may control display 120 to display a UI including a message query about whether there is leg muscle pain (e.g., a UI including a message "You played soccer yesterday. Do your muscles ache?").

In a case in which the step pattern of the user is different from a normal step pattern and a schedule associated with an abnormal step pattern is not included in the schedule information, the processor 150 may determine to display the symptom check UI (e.g., a UI including a message "Your walking strides are different from usual. Are there any problems associated with your leg?") based on only the state information of the user.

The processor 150 may control the communication unit 140 to transmit at least one of the user input and the state information to the symptom check server 200 and/or the hospital server 300, may check the health state of the user based on a symptom check result received from the symptom check server 200 or the hospital server 300 in correspondence to at least one of the user input and the state information, and may set a health state of the user to a second state (e.g., a state in which it is determined that the health state of the user is abnormal) based on the check result. For example, the processor 150 may control communication unit 140 to transmit the user input and the state information to the symptom check server 200 and may receive from the symptom check server 200 a symptom check result indicating a state that the user must go to the hospital. The processor 150 may set the health state of the user to the second state as being a clinic state, based on the symptom check result received from the symptom check server 200.

The processor 150 may set the health state of the user to the second state based on at least one of a user input to the first UI and the state information of the user. The second state may be a state in which the health state of the user is abnormal. For example, in a case in which a user input to the health query UI included in the first UI is a response indicating that the health state of the user is abnormal and a symptom check result that is based on the user input to the symptom check UI and the state information of the user indicating that the user needs treatment, the processor 150 may set the health state of the user to the second state. The second state may be, without limitation, a self-care state, a clinic state, or the like.

The processor 150 may determine a disease or illness of the user and a recovery guide associated with the disease or illness based on at least one of the user input to the first UI and the state information of the user.

The processor 150 may use data stored in the memory 110 upon determining a disease or illness of the user and a recovery guide associated with the disease or illness or upon setting the health state of the user to the second state.

Based on at least one of the user input to the symptom check UI and the state information obtained by the sensor 130, the processor 150 may predict or check the health state of the user.

For example, in a case in which a message of the symptom check UI is "Do you have a headache?", a user input associated with the message is "yes", and a user's temperature value that a temperature sensor measures is 38 degrees C. (100.4 degrees F.), the processor 150 may predict that the health state of the user is "high fever", based on the user's temperature value. As such, in a case of predicting the health state of the user based on the state information obtained by the sensor 130, the processor 150 may predict the health state of the user based on information obtained from a sensor, without separately displaying the symptom check UI. Also, the processor 150 may predict a disease or illness associated with "high fever" based on the health state of the user being "high fever". In a case in which the predicted disease or illness is self-curable, the processor 150 may set the health state of the user to the second state as being the self-care state. In a case in which the predicted disease or illness requires treatment in a hospital, the processor 150 may set the health state of the user to the second state as being the clinical state.

The processor 150 may determine a disease or illness of the user by further using data stored in the memory 110, as well as the user input to the symptom check UI and the state information. For example, genetic information of the user may be included as the data stored in the memory 110. The genetic information may include information indicating that the user experiences a sleep disorder due to low caffeine metabolism of the user even though ingesting a small amount of caffeine.

The processor 150 may determine that a disease of the user is a sleep disorder, based on state information indicating that a sleep time of the user is later than usual and the genetic information stored in the memory 130 (e.g., information indicating that caffeine metabolism of the user is low). In this example, a recovery guide message associated with the disease may be "How does it sound not to drink coffee today?".

Meanwhile, in a case in which the user input to the symptom check UI is a response "I do not feel symptoms.", the processor 150 may display a message associated with the state information of the user (e.g., a message "There is a disparity in your walking pattern. It is recommended to get a check-up if any pain is present").

The processor 150 may display the second UI for health management of the user at least once until the health state of the user set to the second state is set to the first state based on at least one of the user input and the state information of the user. The second UI may include, for example, a UI to provide a recovery guide associated with a disease of the user, a UI to query whether the user is recovered, a UI to query whether to check symptoms, a UI to check symptoms of the user, and the like.

The UI to provide the recovery guide associated with the disease or illness of the user may include a recovery guide determined based on at least one of the user input to the first UI and the state information of the user.

For example, the recovery guide may be a self-care message, a hospital visiting message, or the like. The self-care message may include diet and exercise methods. The hospital visiting message may include a guide associated with a hospital capable of curing or specializing in curing a particular disease or illness.

The processor 150 may also determine a new recovery guide based on at least one of the state information of the user and the user input and may display a UI to provide the new recovery guide. The new recovery guide may be determined and displayed periodically, as well as when the state information of the user changes.

The UI to query whether the user is recovered may include, without limitation, a message to query whether the user is recovered, an object to receive a user input associated with whether the user is recovered (e.g., a touch button), and the like. If state information obtained when the health state of the user is the second state does not satisfy the predefined condition, the processor 150 may control display 120 to display a UI to query whether the user is recovered and may receive a user input to this UI about whether the user is recovered.

The UI to query whether to check symptoms and the UI to check symptoms of the user, which belong to the second UI, are the same as the UI to query whether to check symptoms and the UI to check symptoms of the user, which belong to the first UI, and thus, a detailed description thereof will not be repeated here. The UI to query whether to check symptoms and the UI to check symptoms of the user, which belong to the second UI, may be displayed based on a user input to the UI to query whether the user is recovered and may be displayed periodically.

The processor 150 may check symptoms based on at least one of the state information of the user and the user input; based on the check result, the processor 150 may maintain the health state of the user at the second state or may set the health state of the user to the first state. Also, even though the health state of the user is maintained at the second state, if the second state of the user is the self-care state, the processor 150 may change the second state of the user to the clinic state and vice versa.

Figure 2:
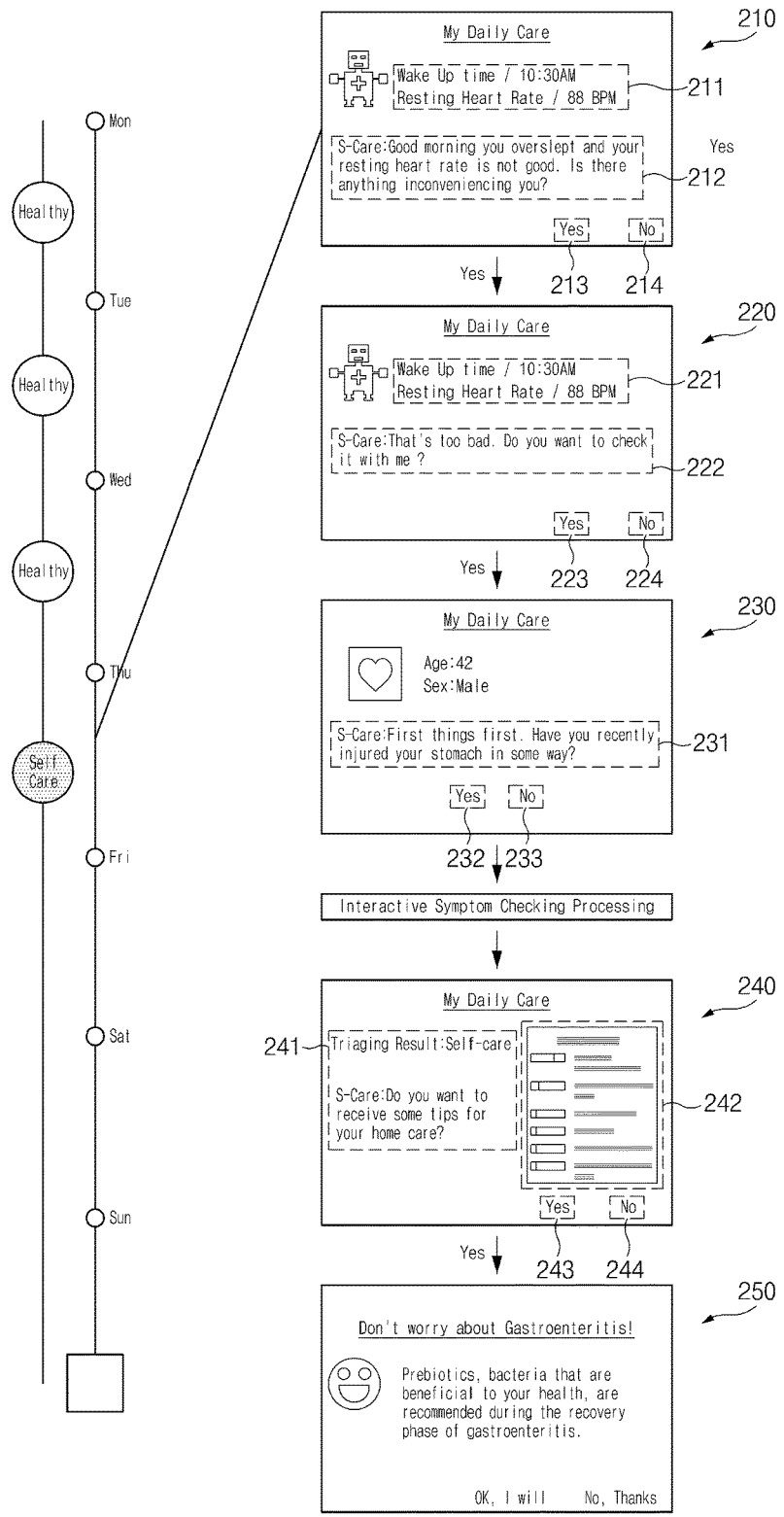
FIG. 2 illustrates an example in which a user decides to check symptoms, a health state of the user is changed from a first state to a second state depending on a symptom check result, and a disease of the user and a recovery guide associated with the disease are provided based on a user input associated with the disease of the user and state information, according to an example embodiment of the present disclosure.
Figure 3:
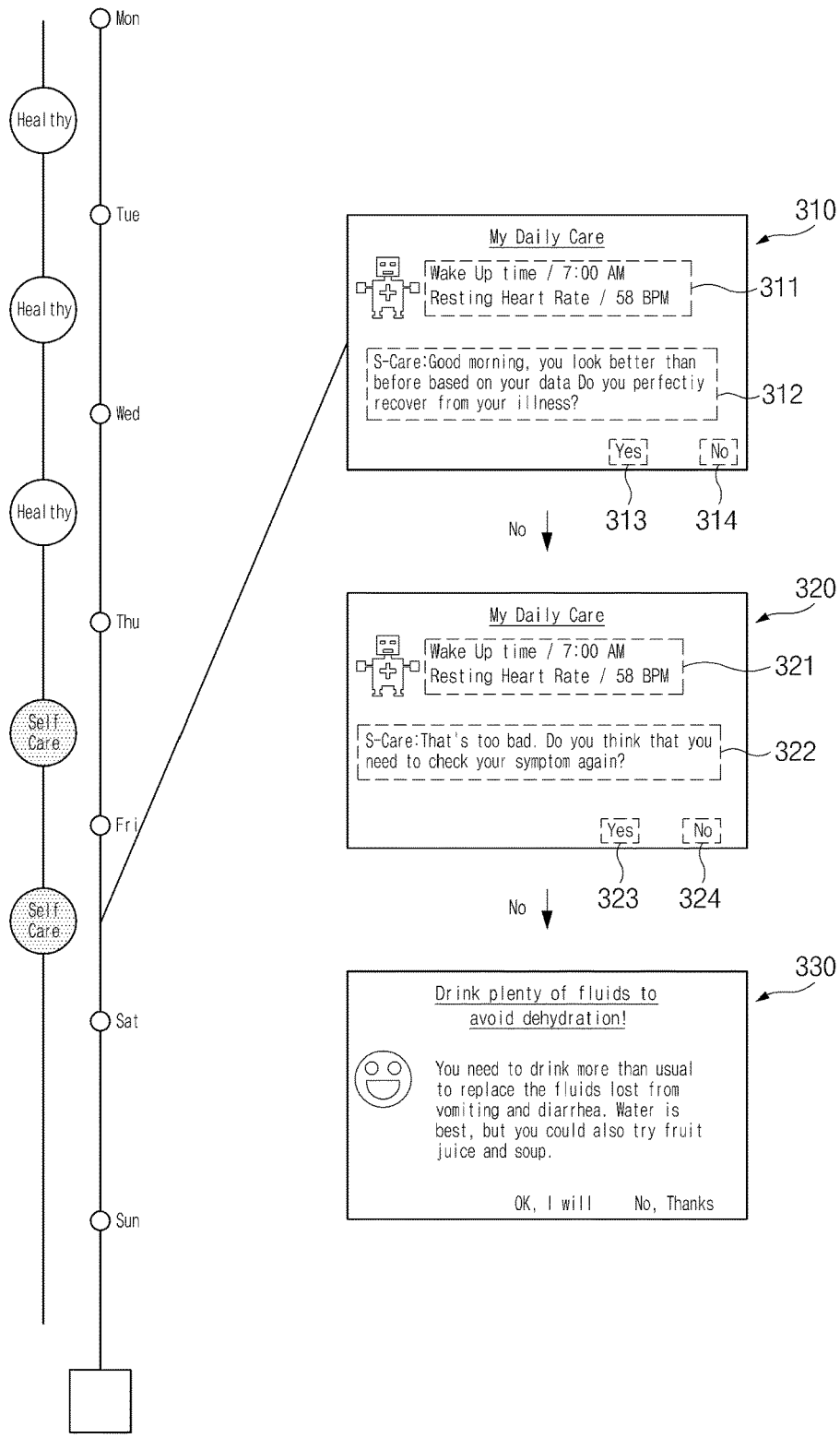
FIG. 3 illustrates an example in which a health state of the user is maintained at the second state, the user decides not to check symptoms, and a guide for health management of the user is provided, according to an example embodiment of the present disclosure.
Figure 4:
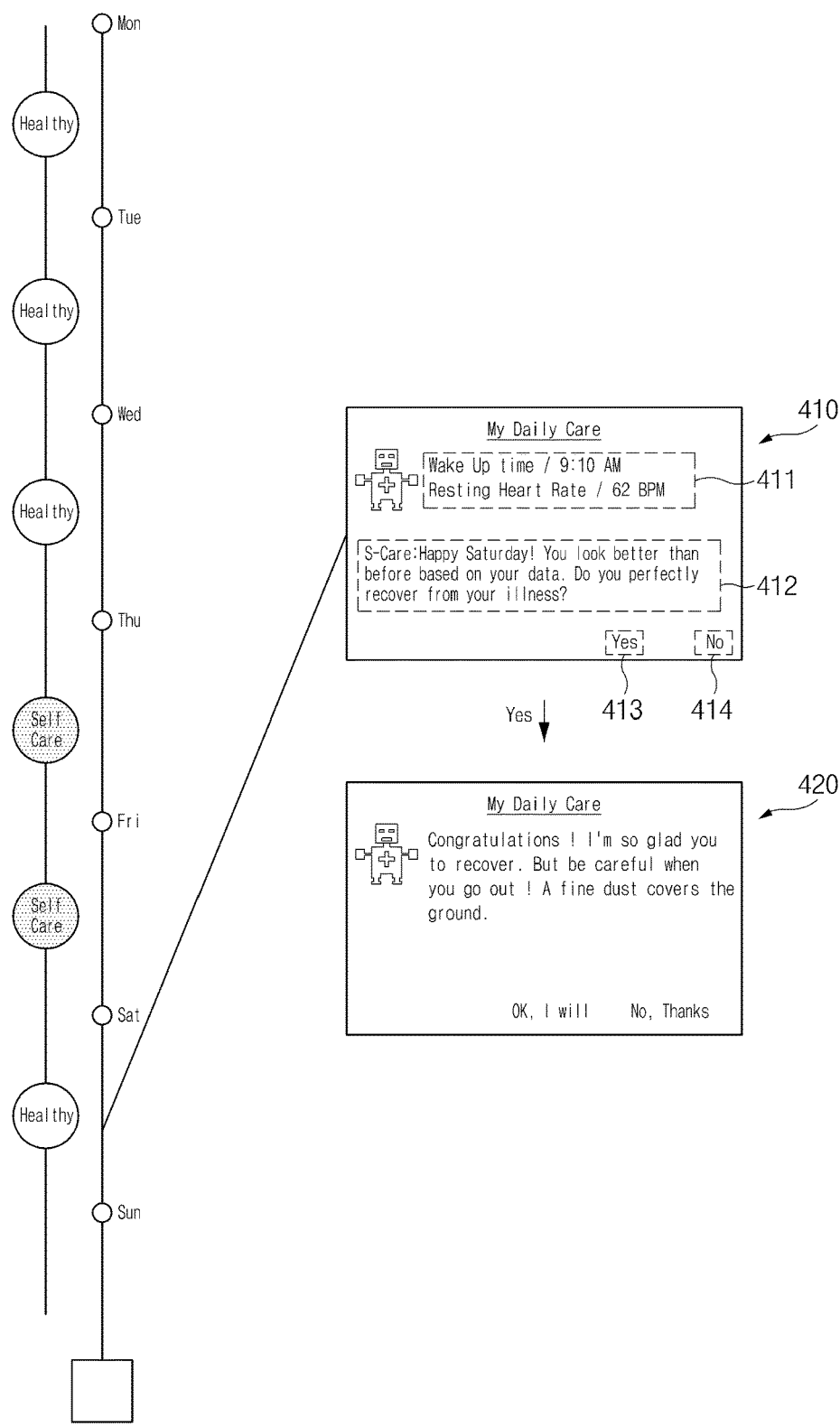
FIG. 4 illustrates an example in which a health state of the user is changed from the second state to the first state, according to an example embodiment of the present disclosure.

FIGS. 2 to 4 illustrate UIs that an electronic device may provide for each case, according to an example embodiment of the present disclosure.

In the non-limiting examples of FIGS. 2 to 4, it is assumed that a user is in a normal state when a weekday wake-up time is between 6 AM to 7 AM, a weekend wake-up time is between 9 AM to 10 AM, and a (resting) heart rate is between 55 to 75 BPM. It is also assumed that a predefined condition is a case in which state information of the user does not correspond to a normal state.

FIG. 2 shows an example in which the user decides to check symptoms, a health state of the user is changed from the first state to the second state depending on a symptom check result, and a disease or illness of the user and a recovery guide associated with the disease or illness are provided based on a user input associated with the disease or illness of the user and state information, according to a non-limiting embodiment of the present disclosure.

Referring to FIG. 2, the health state of the user corresponds to the first state as "Healthy" until Wednesday. State information obtained by the sensor 130 includes information indicating that a weekday (Thursday) wake-up time of the user is 10:30 AM and a resting heart rate is 88 BPM. Because the wake-up time and the heart rate of the user do not correspond to a normal state, the processor 150 may control display 120 to display a health query UI 210 of a first UI on the display 120. As illustrated in FIG. 2, the health query UI 210 of the first UI may include state information 211 of the user, a query message 212 associated with health, and objects (e.g., touch buttons) 213 and 214 to receive user input associated with a response to the query message 212.

Referring to FIG. 2, assuming the user input is response 213 ("Yes") indicating that the health state of the user is abnormal, the processor 150 may control display 120 to display a UI 220 to query whether to check symptoms.

As illustrated in FIG. 2, the UI 220 to query whether to check symptoms may include state information 221 of the user, a query message 222 to query whether to check symptoms, and objects (e.g., touch buttons) 223 and 224 to receive a user input associated with a response to the query message 222.

Referring to FIG. 2, assuming a user input to the UI 220 to query whether to check symptoms is the response 223 to check symptoms ("Yes"), the processor 150 may control display 120 to display a symptom check UI 230. As illustrated in FIG. 2, the symptom check UI 230 may include a message 231 to check symptoms and objects (e.g., touch buttons) 232 and 233 to receive a user input associated with a response to the symptom check. As described above, symptoms to be checked may be determined based on state information of the user or the like in the message 231 to check symptoms.

The processor 150 may control communication unit 140 to transmit at least one of the user inputs to the symptom check UI and the state information to an external server, may set a health state of the user to a second state based on a symptom check result received from the external server in correspondence to at least one of the user input and the state information, and may determine a disease or illness of the user and a recovery guide associated with the disease or illness.

In the example of FIG. 2, depending on the symptom check result based on at least one of the user input and the state information, the processor 150 may determine the health state of the user as the second state being a self-care state and may provide recovery guide UIs 240 and 250 associated with self-care.

The UIs 240 and 250 associated with self-care may include a message 241 to query whether to receive tips associated with self-care, a message 242 indicating a disease or illness of the user, and objects (e.g., touch buttons) 243 and 244 to receive a user input associated with response to the query about whether to receive tips for care. In FIG. 2, assuming the user input associated with whether to receive tips is a response 243 to receive the tips ("Yes"), the tip UI 250 associated with self-care may be provided.

FIG. 3 illustrates an example in which a health state of a user is maintained at a second state, the user decides not to check symptoms, and a guide for health management of the user is provided, according to a non-limiting embodiment of the present disclosure. Referring to FIG. 3, the health state of the user corresponds to the second state as "Self-care" on Thursday. State information obtained by the sensor 130 includes information indicating that a weekday (Friday) wake-up time of the user is 7:00 AM and a heart rate is 58 BPM. Because the wake-up time and the heart rate of the user correspond to a normal state, the processor 150 may control display 120 to display a UI 310 to query whether the user is recovered as a second UI. As illustrated in FIG. 3, the UI 310 to query whether the user is recovered may include state information 311 of the user, a message 312 to query whether the user is recovered, and objects (e.g., touch buttons) 313 and 314 to receive a user input associated with a response to the query about whether the user is recovered.

Referring to FIG. 3, assuming the user input is the response 314 indicating that the health state of the user is abnormal ("No"), the processor 150 may maintain a health state of the user at the second state based on the user input.

The processor 150 may control display 120 to display the UI 320 to query whether to check symptoms. As illustrated in FIG. 3, the UI 320 to query whether to check symptoms of the user may include state information 321 of the user, a message 322 to query whether to check symptoms, and objects (e.g., touch buttons) 323 and 324 to receive a user input associated a response to the query about whether to check symptoms.

Referring to FIG. 3, assuming the user input is the response 324 not to check symptoms ("No"), the processor 150 may control display 120 to display a guide 330 for health management of the user. For example, as illustrated in FIG. 3, the processor 150 may control display 120 to provide a guide message "You need to drink more water".

FIG. 4 illustrates an example in which a health state of a user is changed from a second state to a first state, according to a non-limiting embodiment of the present disclosure.

Referring to FIG. 4, the health state of the user corresponds to the second state as "Self-care" on Friday. State information obtained by the sensor 130 includes information indicating that a weekend (Saturday) wake-up time of the user is 9:10 AM and a heart rate is 62 BPM. Because the wake-up time and the heart rate of the user correspond to a normal state, the processor 150 may control display 120 to display a UI 410 to query whether the user is recovered as a second UI. As illustrated in FIG. 4, the UI 410 to query whether the user is recovered may include state information 411 of the user, a message 412 to query whether the user is recovered, and objects (e.g., touch buttons) 413 and 414 to receive a user input associated with a response to the query about whether the user is recovered.

Referring to FIG. 4, assuming the user input is the response 413 indicating that the health state of the user is normal ("Yes"), the processor 150 may change a health state of the user to the first state. In this case, the processor 150 may determine the health state of the user based further on state information of the user.

The processor 150 may change the health state of the user to the first state and may provide a UI 420 including a message associated with a state change of the user.

Figure 5:
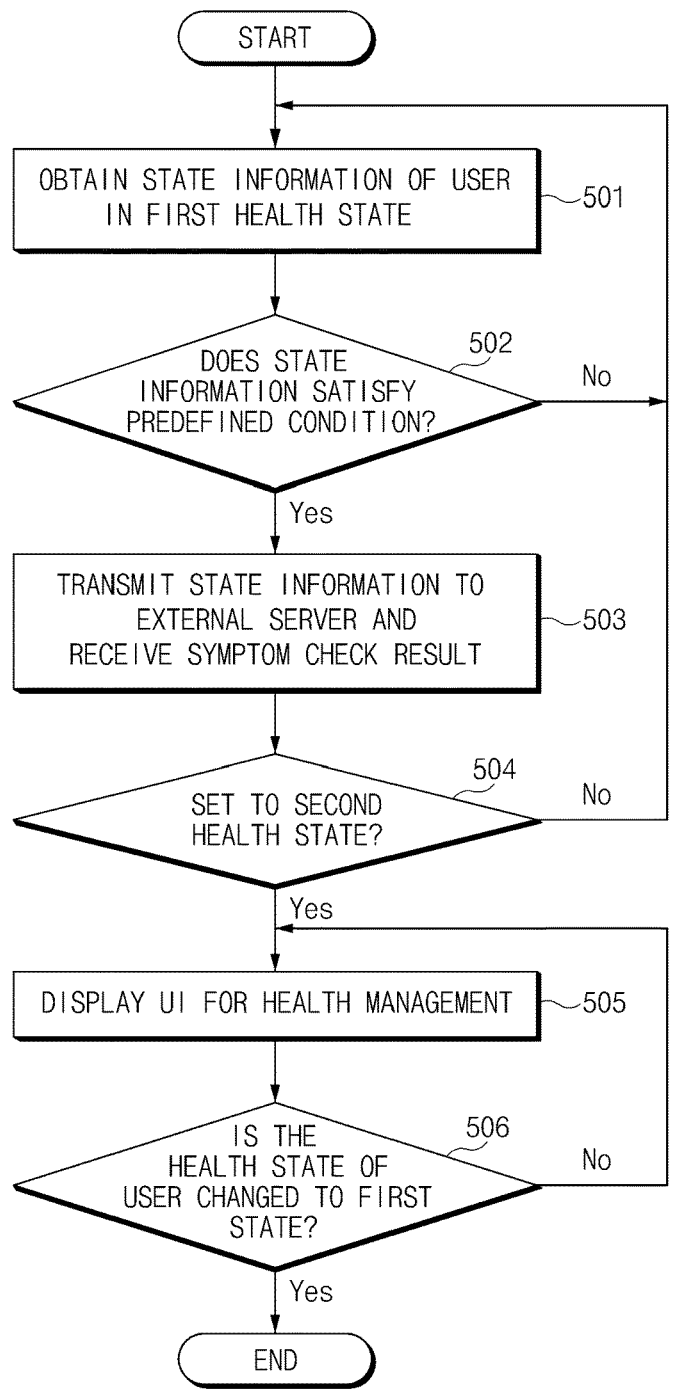
FIG. 5 is a flowchart illustrating an example user health management method of the electronic device according to an example embodiment of the present disclosure.

FIG. 5 is a flowchart illustrating a user health management method of the electronic device 100 according to an embodiment of the present disclosure.

Referring to FIG. 5, the user health management method of the electronic device 100 according to an example embodiment of the present disclosure may include operations of obtaining state information of a user (501), determining whether the state information satisfies a predetermined condition (502), transmitting state information to an external server and receiving a symptom check result (503), determining whether to set a health state of the user to a second state (504), displaying a second UI (505), and determining whether the health state of the user changes to the first state (506).

In operation 501, the electronic device 100 may obtain the state information of a user in the first state. For example, the at least one sensor 130 may obtain information such as a heart rate and a sleep time of the user. Additionally, in operation 501, the electronic device 140 may receive context information.

In operation 502, the electronic device 100 may determine whether state information obtained when the health state of the user corresponds to the first state satisfies a predefined condition. If the obtained state information satisfies the predefined condition, in operation 503, the processor 150 may control communication unit 140 to transmit the state information to an external server, such as the symptom check server 200 and/or the hospital server 300, and may receive a symptom check result. If the obtained state information does not satisfy the predefined condition in operation 502, the electronic device 100 may continue to continuously monitor the health state of the user.

The first state may be a state in which the health state of the user is normal. The first state may be defined by the processor 150 based on the state information of the user. For example, the processor 150 may determine the normal state of the user based on state information obtained by the at least one sensor 130 during a specified time period (e.g., hours, days, weeks, months, etc.). In this example, the predefined condition may include a case in which the obtained state information does not correspond to a normal state.

The predefined condition may be defined based on the context information obtained by the communication unit 140 and the user's state information obtained by the sensor 130.

In operation 504, the processor 150 determines whether to set the user's health state to the second state based on at least one of the symptom check result and the state information. If the state is changed, the processor 150 proceeds to operation 505. If the state is not changed, the electronic device 100 may continue to continuously monitor the health state of the user.

In operation 505 and operation 506, the processor 150 may provide a second UI at least once and may provide the second UI for health management of the user until the health state of the user changes from the second state to the first state.

The second UI may include a UI to provide a recovery guide associated with a disease or illness of the user, a UI to query whether the user is recovered, a UI to query whether to check symptoms, a UI to check symptoms of the user, and the like.

In a case in which the health state of the user is the second state, the processor 150 may, for example, provide recovery guides 240 and 250 associated with a disease or illness that is determined based on at least one of a user input to the symptom check UI 230 and the state information.

If the state information obtained when the health state of the user is the second state does not satisfy the predefined condition, the processor 150 may control display 120 to display a UI 410 to query whether the user is recovered. The processor 150 may set the health state of the user to the first state based on at least one of the state information and a user input to the UI 410 to query whether the user is recovered.

If the health state of the user is changed to the first state, the processor 150 may stop providing the second UI.

Figure 6A:
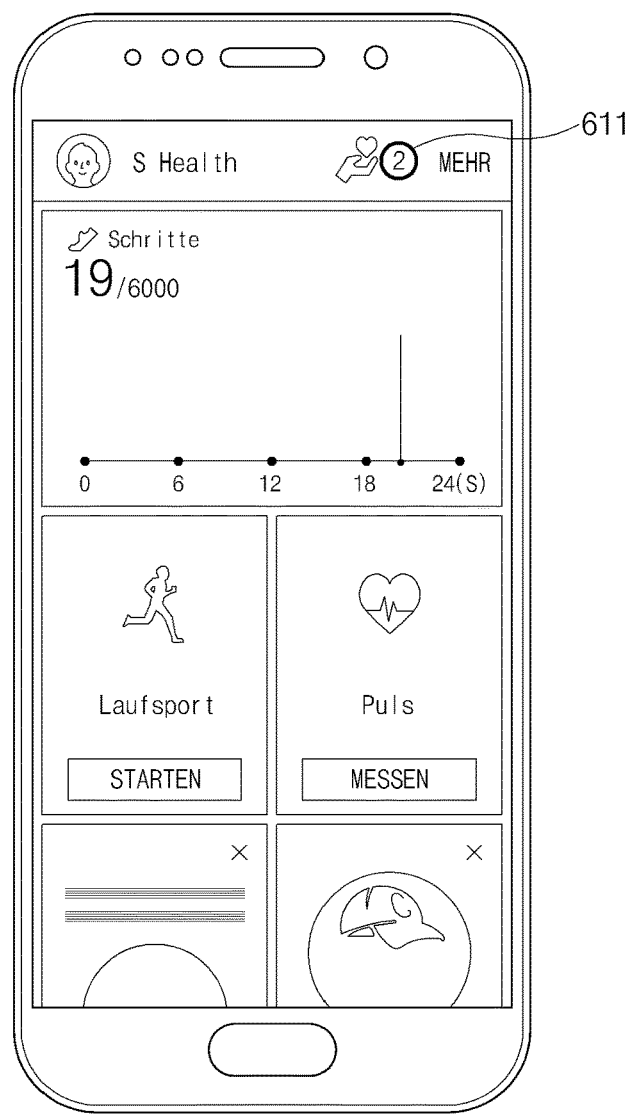
FIGS. 6A and 6B illustrate how an example UI is displayed in a display of the electronic device, according to an example embodiment of the present disclosure.
Figure 6B:
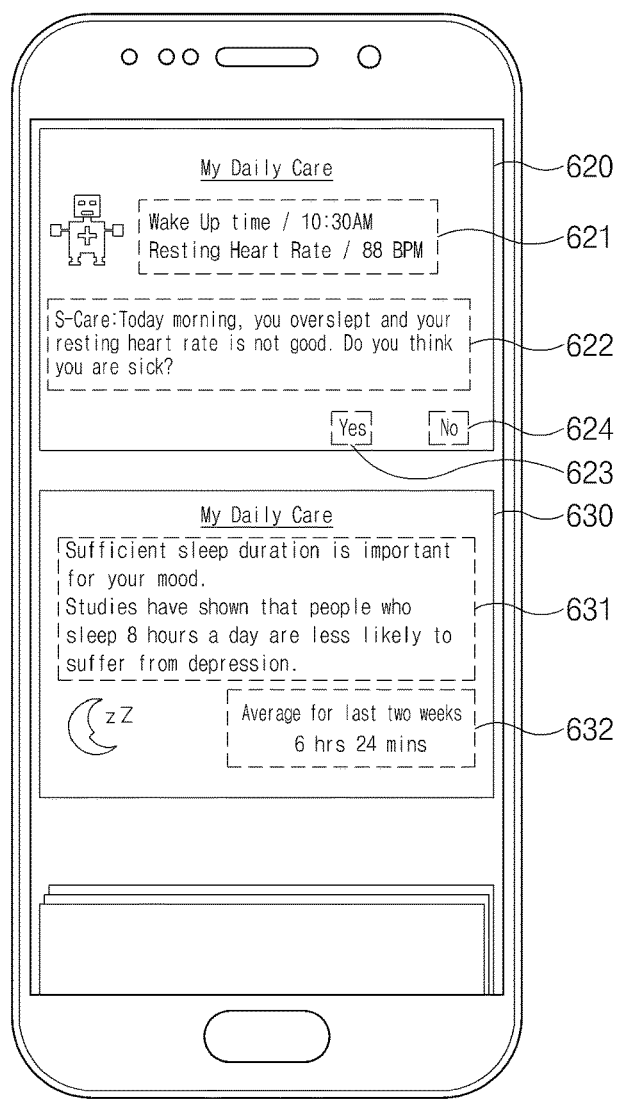

FIGS. 6A and 6B illustrate how a UI is displayed in a display of an electronic device, according to an example embodiment of the present disclosure.

In a case in which there is a first UI or a second UI to be displayed, the processor 150 may control display 120 to display a number indicating a number of undisplayed first and second UIs before displaying the first UI or the second UI on the display 120.

For example, in a case in which the first UI that the processor 150 will display and a UI to be displayed for health management of a user exist when state information obtained by the sensor 130 satisfies a predefined condition, as illustrated in FIG. 6A, the processor 150 may display the number of UIs not displayed with an icon 611 before displaying a UI on the display 120.

The icon 611 displayed on the display 120 may be an object to receive a user input for displaying a UI. The processor 150 may control display 120 to display one or more UIs in response to a user input to icon 611.

As illustrated in FIG. 6B, the processor 150 may control display 120 to display a plurality UIs 620 and 630 on one screen. The processor 150 may arrange a plurality UIs depending on a created time order, priorities according to a set condition, or the like.

Also, as described above, the UIs 620 and 630 displayed on the display 120 may include state information 621 and 632 of the user, messages 622 and 631, objects 623 and 624 to receive a user input, and the like.

Figure 7:
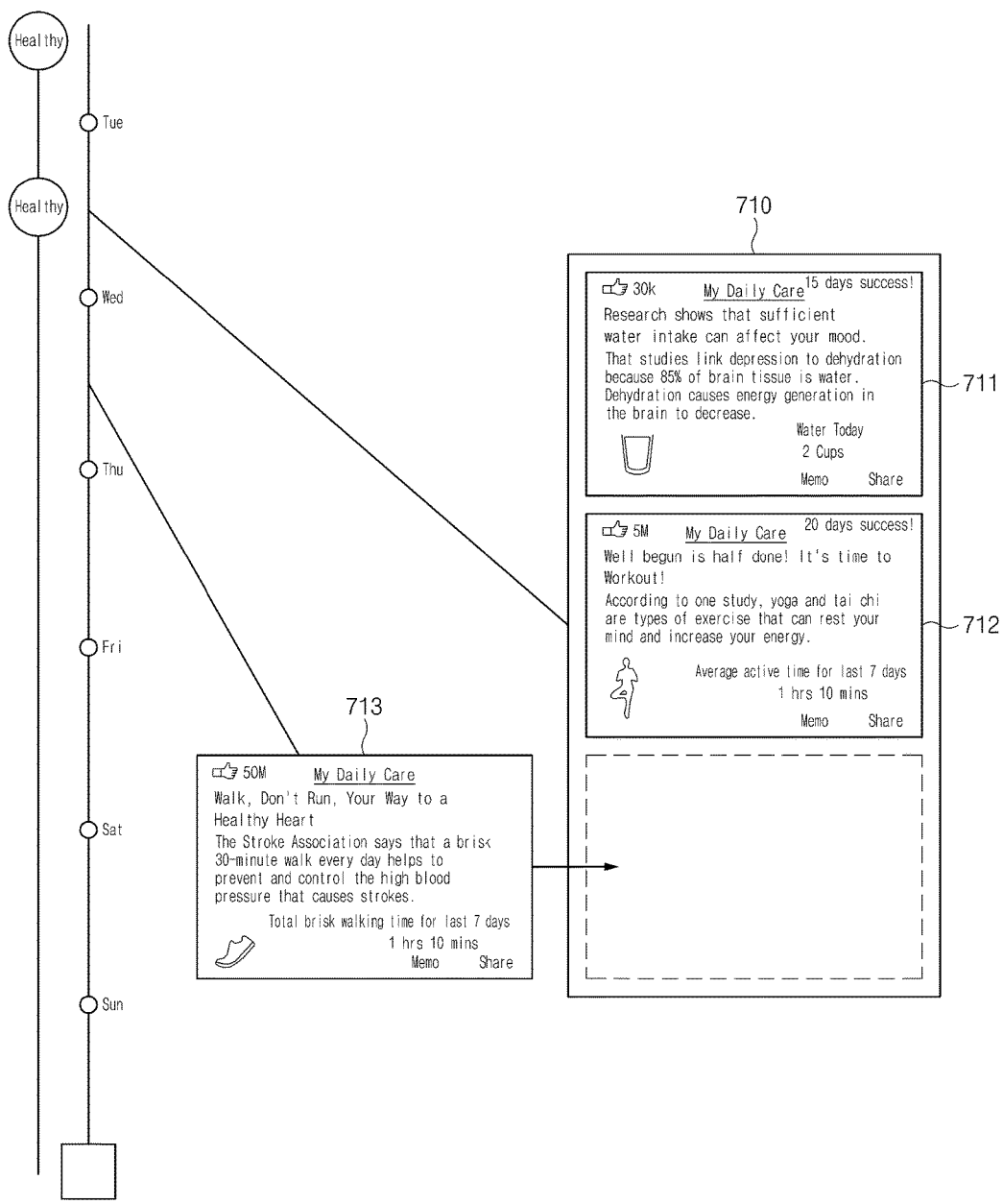
FIG. 7 illustrates how an example guide for health management is further stored in a memory, according to an example embodiment of the present disclosure.

FIG. 7 illustrates how a guide for health management is further stored in a memory, according to an example embodiment of the present disclosure.

As illustrated in FIG. 7, one or more guides 711 and 712 for health management may be stored in a memory 710. The memory 710 of FIG. 7 may correspond to the memory 110 of FIG. 1.

The processor 150 may create a guide 713 for health management and may store the created guide 713 for health management in the memory 710. The guides 711, 712, and 713 for health management may be stored in a specific folder of the memory 710 and may be displayed under control of the processor 150.

For example, as illustrated in FIG. 7, the processor 150 may create the guide 711 for health management associated with water, based on a record of "User drank 2 glasses of water on Tuesday". The processor 150 may create the guide 712 for health management associated with a workout, based on a record of "The user's average activity time over the past 7 days is 1:10". The processor 150 may store the created guides 711 and 712 for health management in the memory 710.

The processor 150 may create the guide 713 for health management associated with active walking, based on a record of "The total active walking time over the last 7 days is 1:10". The processor 150 may store the created guide 713 for health management in the memory 710. The processor 150 may store the guide 713 for health management stored on Wednesday in the same folder as the guides 711 and 712 for health management stored on Tuesday.

Figure 8:
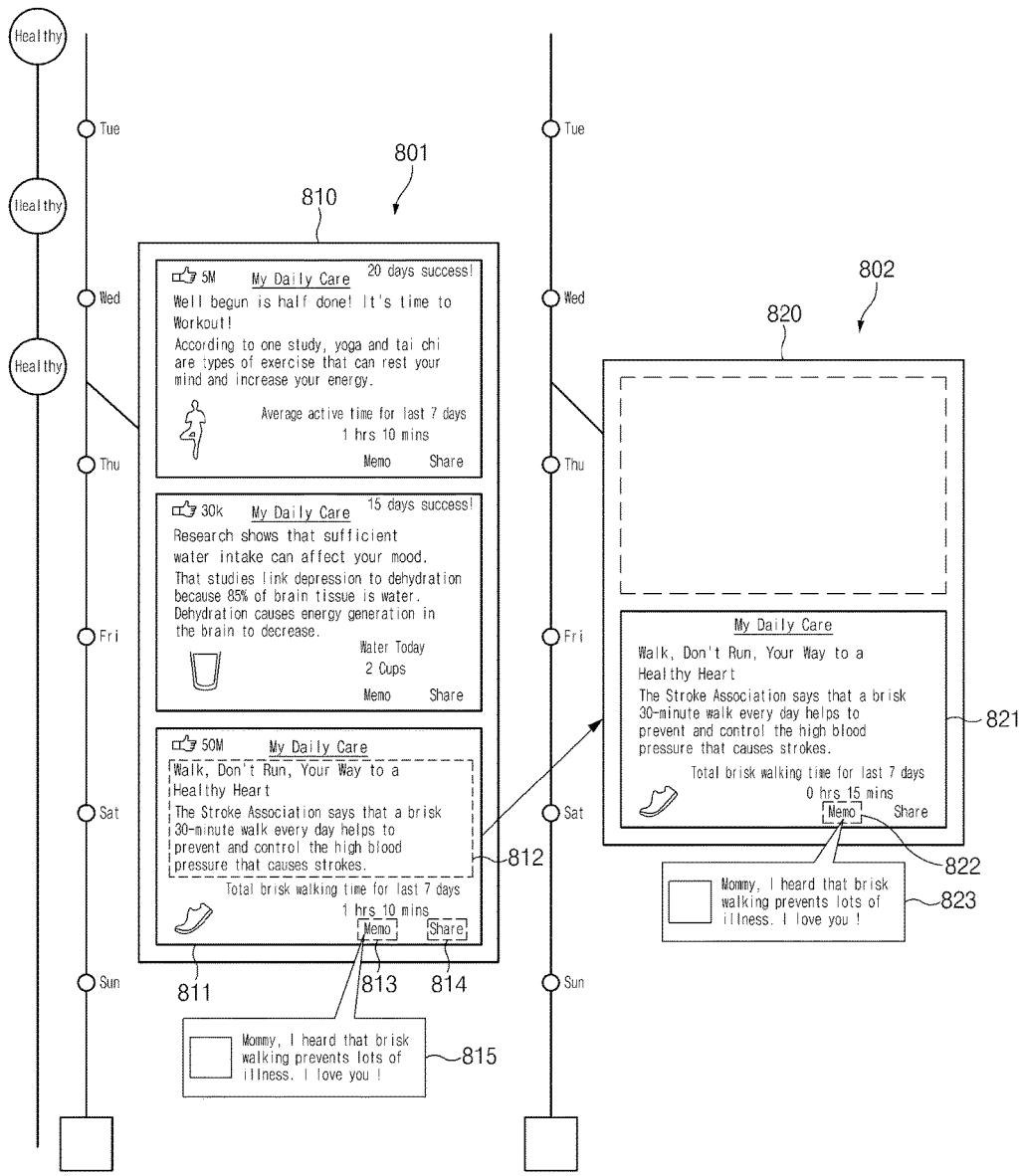
FIG. 8 illustrates how an example guide for health management is transmitted, according to an example embodiment of this disclosure.

FIG. 8 illustrates how a guide for health management is transmitted, according to an example embodiment of this disclosure.

Referring to FIG. 8, one or more guides for health management may be stored in a memory 810 of a first electronic device 801 and a memory 820 of a second electronic device 802. The memories 810 and 820 of FIG. 8 may correspond to the memory 110 of FIG. 1.

A processor of the first electronic device 801 may display a guide UI for health management on a display. A guide UI 811 for health management may include a guide message 812 for health management, an object 813 for receiving an input for creating a memo, and an object 814 for receiving a guide transmission input.

The processor of the first electronic device 801 may store an input memo 815 in the memory 810 together with the guide message 812 for health management in response to a memo input through the object 813 for receiving a memo input. Also, the processor of the first electronic device 801 that transmits a guide may transmit the guide message 812 for health management to the second electronic device 802 through a communication unit in response to a guide transmission input through the object 814 for receiving the guide transmission input. In a case in which the memo 815 is stored together with the guide message 812 for health management, the processor of the first electronic device 801 that transmits a guide may transmit the memo 815 together with the guide message 812 for health management in response to the guide transmission input.

A processor of the second electronic device 802 that receives the guide may receive a guide message 821 for health management through a communication unit. In a case in which the memo 815 is transmitted together with the guide message 812 for health management, the processor of the second electronic device 802 may receive the guide message 821 together with the memo 823. The processor of the second electronic device 802 may store the received guide message for health management and the received memo 823 in the memory 820. Accordingly, a message for health management and a memo may be shared.

The processor of the second electronic device 802 that receives the guide may display a guide UI 821 for health management including the received guide message on a display. The guide UI 821 for health management may include an object 822 for receiving a memo verification input. The processor of the second electronic device 802 may display the received memo 823 together with the guide message for health management on the display in response to the memo verification input.

Figure 9:
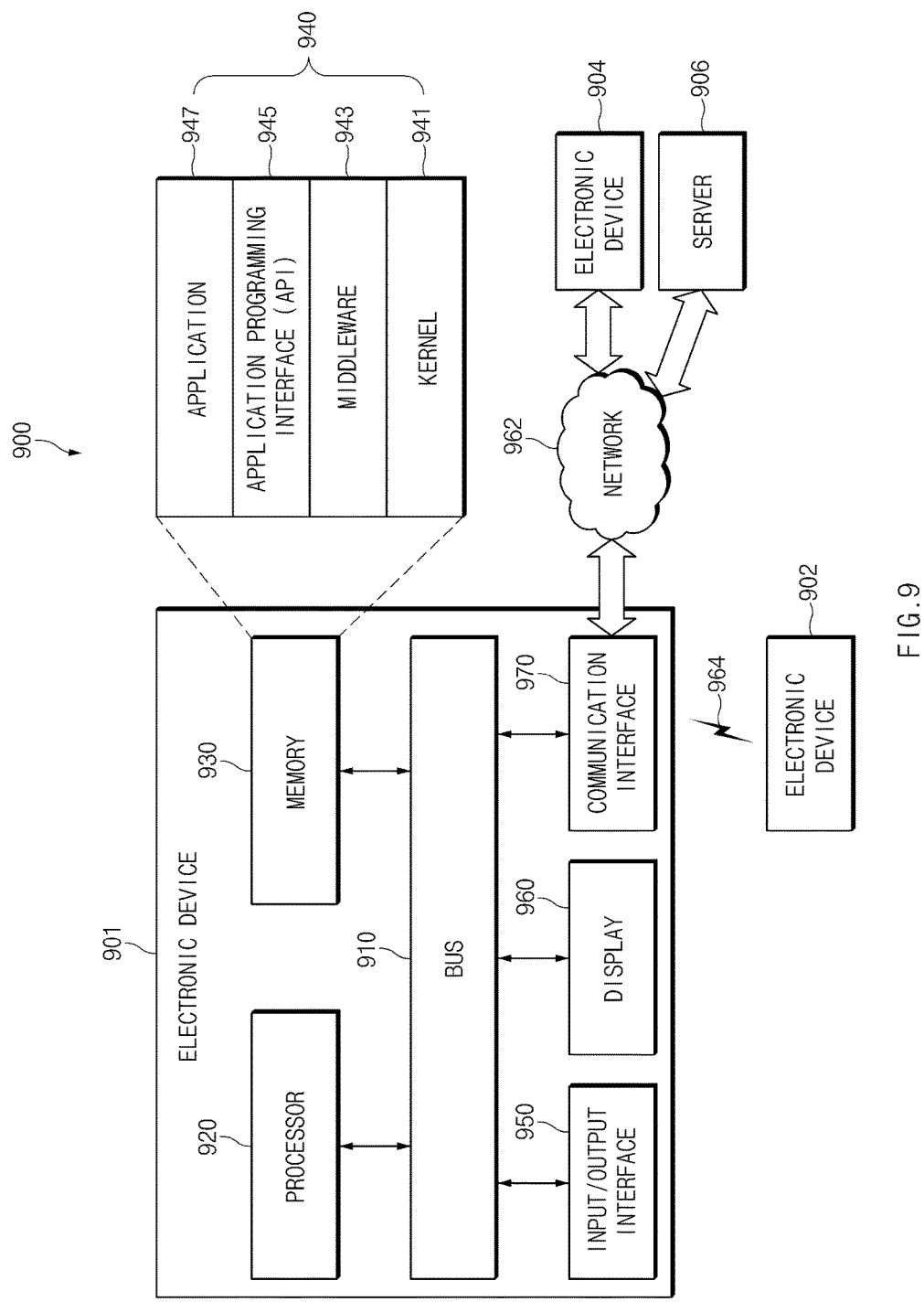
FIG. 9 is a view illustrating an example electronic device in a network environment according to an example embodiment of the present disclosure.

FIG. 9 is a block diagram of an electronic device according to an example embodiment.

Referring to FIG. 9, according to various example embodiments, an electronic device 901 in a network environment is described. The electronic device 901 may include a bus 910, a processor 920, a memory 930, an input/output interface 950, a display 960, and a communication interface 970. According to an example embodiment, the electronic device 901 may not include one or more of the above-described elements or may further include other element(s). The bus 910 may interconnect the above-described elements 920 to 970 and may include circuitry for conveying communications (e.g., a control message and/or data) among the above-described elements. The processor 920 may include one or more of a central processing unit (CPU), an application processor (AP), or a communication processor (CP). For example, the processor 920 may perform an arithmetic operation or data processing associated with control and/or communication for at least other elements of the electronic device 901.

The memory 930 may include a volatile and/or nonvolatile memory. For example, the memory 930 may store instructions or data associated with at least one other element(s) of the electronic device 901. According to an example embodiment, the memory 930 may store software and/or a program(s) 940. The program(s) 940 may include, for example, a kernel 941, middleware 943, an application programming interface (API) 945, and/or an application program (or "an application") 947. At least a part of the kernel 941, the middleware 943, and/or the API 945 may be referred to as an "operating system (OS)". For example, the kernel 941 may control or manage system resources (e.g., the bus 910, the processor 920, the memory 930, and the like) that are used to execute operations or functions of other programs (e.g., middleware 943, the API 945, and the application program 947). Furthermore, the kernel 941 may provide an interface that allows the middleware 943, the API 945, or the application program 947 to access discrete elements of the electronic device 901 so as to control or manage system resources.

The middleware 943 may perform, for example, a mediation role such that the API 945 or the application program 947 communicates with the kernel 941 to exchange data. Furthermore, the middleware 943 may process one or more task requests received from the application program 947 according to a priority. For example, the middleware 943 may assign the priority, which makes it possible to use a system resource (e.g., the bus 910, the processor 920, the memory 930, or the like) of the electronic device 901, to at least one of the application program 947 and may process the one or more task requests. The API 945 may be an interface through which the application program 947 controls a function provided by the kernel 941 or the middleware 943, and may include, for example, at least one interface or function (e.g., an instruction) for file control, window control, image processing, character control, or the like. The input/output interface 950 may include circuitry for transmitting an instruction or data input from a user or another external device, to other element(s) of the electronic device 901 or may output an instruction or data, received from other element(s) of the electronic device 901, to a user or another external device.

The display 960 may include, for example, a liquid crystal display (LCD), a light-emitting diode (LED) display, an organic LED (OLED) display, a microelectromechanical systems (MEMS) display, or an electronic paper display. The display 960 may display, for example, various contents (e.g., a text, an image, a video, an icon, a symbol, and the like) to a user. The display 960 may include a touch screen and may receive, for example, a touch, gesture, proximity, or hovering input using an electronic pen or a part of a user's body. For example, the communication interface 970 may include circuitry for establishing communication between the electronic device 901 and an external device (e.g., the first electronic device 902, the second electronic device 904, or the server 906). For example, the communication interface 970 may be connected to the network 962 over wireless communication or wired communication to communicate with the external device(s) (e.g., the second electronic device 904 or the server 906).

For example, the wireless communication may include cellular communication using at least one of long-term evolution (LTE), LTE Advanced (LTE-A), Code Division Multiple Access (CDMA), Wideband CDMA (WCDMA), Universal Mobile Telecommunications System (UMTS), Wireless Broadband (WiBro), Global System for Mobile Communications (GSM), or the like. The wireless communication may include at least one of wireless fidelity (Wi-Fi), Bluetooth, Bluetooth low energy (BLE), Zigbee, near field communication (NFC), magnetic stripe transmission (MST), radio frequency (RF), a body area network, or the like. According to an example embodiment, the wireless communication may include GNSS. GNSS may be one of, for example, a global positioning system (GPS), a global navigation satellite system (Glonass), a Beidou navigation satellite system (hereinafter referred to as "Beidou"), or an European global satellite-based navigation system (hereinafter referred to as "Galileo"). Hereinafter, in this disclosure, "GPS" and "GNSS" may be interchangeably used. The wired communication may include, without limitation, at least one of, for example, a universal serial bus (USB), a high definition multimedia interface (HDMI), a recommended standard-1032 (RS-1032), powerline communication, a plain old telephone service (POTS), or the like. The network 962 may include at least one of telecommunications networks, for example, a computer network (e.g., LAN or WAN), an Internet, or a telephone network.

Each of the first and second external electronic devices 902 and 904 may be a device of which the type is different from or the same as that of the electronic device 901. According to various example embodiments, all or a portion of operations that the electronic device 901 will perform may be executed by another or plural electronic devices (e.g., the first electronic device 902, the second electronic device 904 or the server 906). According to an example embodiment, in a case in which the electronic device 901 executes any function or service automatically or in response to a request, the electronic device 901 may not perform the function or the service internally, but, alternatively and/or additionally, it may request at least a portion of a function associated with the electronic device 901 at other electronic device (e.g., the electronic device 902 or 904 or the server 906). The other electronic device (e.g., the electronic device 902 or 904 or the server 906) may execute the requested function or additional function and may transmit the execution result to the electronic device 901. The electronic device 901 may provide the requested function or service using the received result or may additionally process the received result to provide the requested function or service. To this end, for example, cloud computing, distributed computing, or client-server computing may be used.

Figure 10:
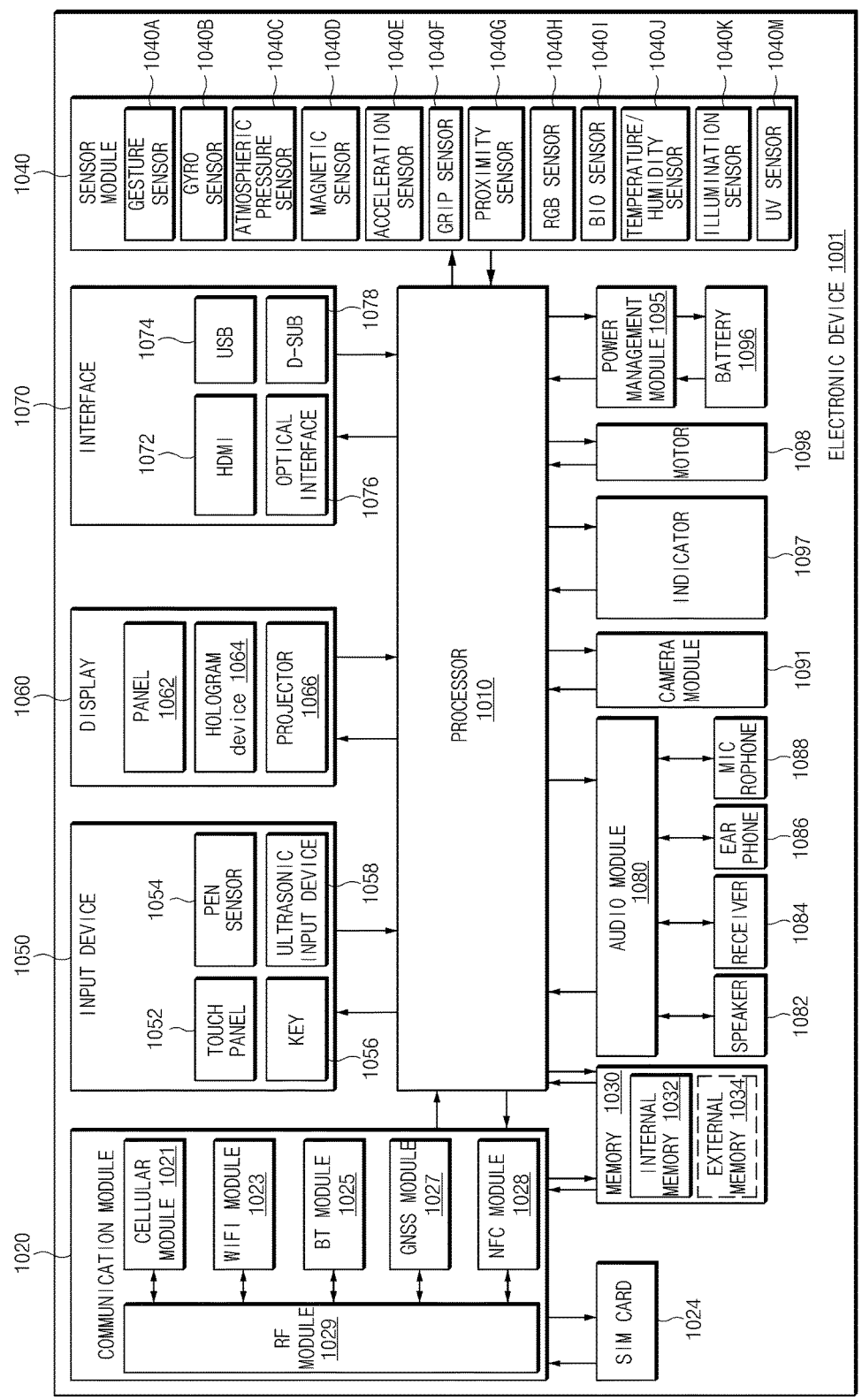
FIG. 10 is a block diagram of an example electronic device according to an example embodiment of the present disclosure.

FIG. 10 illustrates a block diagram of an electronic device, according to an example embodiment. An electronic device 1001 may include, for example, all or a part of the electronic device 901 illustrated in FIG. 9. The electronic device 1001 may include one or more processors (e.g., an application processor (AP)) 1010, a communication module 1020, a subscriber identification module(s) 1024, a memory (ies) 1030, a sensor module 1040, an input device(s) 1050, a display(s) 1060, an interface(s) 1070, an audio module 1080, a camera module 1091, a power management module 1095, a battery 1096, an indicator 1097, and a motor 1098. For example, the processor 1010 may be implemented with a System on Chip (SoC). According to an example embodiment, the processor 1010 may further include a graphic processing unit (GPU) and/or an image signal processor. The processor 1010 may include at least a part (e.g., a cellular module 1021) of elements illustrated in FIG. 10. The processor 1010 may load an instruction or data, which is received from at least one of other elements (e.g., a nonvolatile memory), into a volatile memory and process the loaded instruction or data. The processor 1010 may store result data in the nonvolatile memory.

The communication module 1020 may be configured the same as or similar to the communication interface 970 of FIG. 9. The communication module 1020 may include the cellular module 1021, a Wi-Fi module 1023, a Bluetooth (BT) module 1025, a GNSS module 1027, a near field communication (NFC) module 1028, and a radio frequency (RF) module 1029. The cellular module 1021 may provide, for example, voice communication, video communication, a character service, an Internet service, or the like over a communication network. According to an example embodiment, the cellular module 1021 may perform discrimination and authentication of the electronic device 1001 within a communication network by using the subscriber identification module (e.g., a SIM card) 1024. According to an example embodiment, the cellular module 1021 may perform at least a portion of functions that the processor 1010 provides. According to an example embodiment, the cellular module 1021 may include a communication processor (CP). According to an example embodiment, at least a part (e.g., two or more) of the cellular module 1021, the Wi-Fi module 1023, the BT module 1025, the GNSS module 1027, or the NFC module 1028 may be included within one Integrated Circuit (IC) or an IC package. For example, the RF module 1029 may transmit and receive a communication signal (e.g., an RF signal). For example, the RF module 1029 may include a transceiver, a power amplifier module (PAM), a frequency filter, a low noise amplifier (LNA), an antenna, or the like. According to another example embodiment, at least one of the cellular module 1021, the Wi-Fi module 1023, the BT module 1025, the GNSS module 1027, or the NFC module 1028 may transmit and receive an RF signal through a separate RF module. The subscriber identification module 1024 may include, for example, a card and/or embedded SIM that includes a subscriber identification module and may include unique identifier information (e.g., integrated circuit card identifier (ICCID)) or subscriber information (e.g., international mobile subscriber identity (IMSI)).

The memory 1030 (e.g., the memory 930) may include an internal memory 1032 or an external memory 1034. For example, the internal memory 1032 may include, without limitation, at least one of a volatile memory (e.g., a dynamic random access memory (DRAM), a static RAM (SRAM), a synchronous DRAM (SDRAM), or the like), a nonvolatile memory (e.g., a one-time programmable read only memory (OTPROM), a programmable ROM (PROM), an erasable and programmable ROM (EPROM), an electrically erasable and programmable ROM (EEPROM), a mask ROM, a flash ROM, a flash memory, a hard drive, or a solid state drive (SSD). The external memory 1034 may include, without limitation, a flash drive such as compact flash (CF), secure digital (SD), micro secure digital (Micro-SD), mini secure digital (Mini-SD), extreme digital (xD), a multimedia card (MMC), a memory stick, or the like. The external memory 1034 may be operatively and/or physically connected to the electronic device 1001 through various interfaces.

The sensor module 1040 may measure, for example, a physical quantity or may detect an operation state of the electronic device 1001. The sensor module 1040 may convert the measured or detected information to an electric signal. For example, the sensor module 1040 may include at least one of a gesture sensor 1040A, a gyro sensor 1040B, a barometric (atmospheric) pressure sensor 1040C, a magnetic sensor 1040D, an acceleration sensor 1040E, a grip sensor 1040F, a proximity sensor 1040G, a color sensor 1040H (e.g., red, green, blue (RGB) sensor), a biometric sensor 1040I, a temperature/humidity sensor 1040J, an illuminance sensor 1040K, or an UV sensor 1040M. Although not illustrated, additionally or generally, the sensor module 1040 may further include, for example and without limitation, an E-nose sensor, an electromyography (EMG) sensor, an electroencephalogram (EEG) sensor, an electrocardiogram (ECG) sensor, an infrared (IR) sensor, an iris sensor, and/or a fingerprint sensor. The sensor module 1040 may further include a control circuit for controlling at least one or more sensors included therein. According to an example embodiment, the electronic device 1001 may further include a processor that is a part of the processor 1010 or independent of the processor 1010 and is configured to control the sensor module 1040. The processor may control the sensor module 1040 while the processor 1010 remains at a sleep state.

The input device 1050 may include, for example, a touch panel 1052, a (digital) pen sensor 1054, a key 1056, or an ultrasonic input unit 1058. For example, the touch panel 1052 may use at least one of capacitive, resistive, infrared and ultrasonic detecting methods. Also, the touch panel 1052 may further include a control circuit. The touch panel 1052 may further include a tactile layer to provide a tactile reaction to a user. The (digital) pen sensor 1054 may be, for example, a part of a touch panel or may include an additional sheet for recognition. The key 1056 may include, for example, a physical button, an optical key, or a keypad. The ultrasonic input device 1058 may detect (or sense) an ultrasonic signal, which is generated from an input device, through a microphone (e.g., a microphone 1088) and may check data corresponding to the detected ultrasonic signal.

The display 1060 (e.g., the display 960) may include a panel 1062, a hologram device 1064, a projector 1066, and/or a control circuit for controlling the panel 1062, the hologram device 1064, or the projector 1066. The panel 1062 may be implemented, for example, to be flexible, transparent or wearable. The panel 1062 and the touch panel 1052 may be integrated into a single module. According to an example embodiment, the panel 1062 may include a pressure sensor (or force sensor) that measures the intensity of touch pressure by a user. The pressure sensor may be implemented integrally with the touch panel 1052, or may be implemented as at least one sensor separately from the touch panel 1052. The hologram device 1064 may display a stereoscopic image in a space using a light interference phenomenon. The projector 1066 may project light onto a screen so as to display an image. For example, the screen may be arranged in the inside or the outside of the electronic device 1001.

The interface 1070 may include, for example, a high-definition multimedia interface (HDMI) 1072, a universal serial bus (USB) 1074, an optical interface 1076, or a D-subminiature (D-sub) 1078. The interface 1070 may be included, for example, in the communication interface 970 illustrated in FIG. 9. Additionally or generally, the interface 1070 may include, for example and without limitation, a mobile high definition link (MHL) interface, a SD card/multi-media card (MMC) interface, or an infrared data association (IrDA) standard interface.

The audio module 1080 may convert a sound and an electric signal in dual directions (i.e., bi-directionally). At least a part of the audio module 1080 may be included, for example, in the input/output interface 950 illustrated in FIG. 9. The audio module 1080 may process, for example, sound information that is input or output through a speaker 1082, a receiver 1084, an earphone 1086, or microphone 1088. For example, the camera module 1091 may shoot a still image or a video. According to an example embodiment, the camera module 1091 may include at least one or more image sensors (e.g., a front sensor or a rear sensor), a lens, an image signal processor (ISP), or a flash (e.g., an LED or a xenon lamp). The power management module 1095 may manage, for example, power of the electronic device 1001. According to an example embodiment, a power management integrated circuit (PMIC), a charger IC, or a battery or fuel gauge may be included in the power management module 1095. The PMIC may have a wired charging method and/or a wireless charging method. The wireless charging method may include, for example, a magnetic resonance method, a magnetic induction method or an electromagnetic method and may further include an additional circuit, for example, a coil loop, a resonant circuit, a rectifier, or the like. The battery gauge may measure, for example, a remaining capacity of the battery 1096 and a voltage, current or temperature thereof while the battery is charged. The battery 1096 may include, for example, a rechargeable battery and/or a solar battery.

The indicator 1097 may display a specific state of the electronic device 1001 or a part thereof (e.g., the processor 1010), such as a booting state, a message state, a charging state, and the like. The motor 1098 may convert an electrical signal into a mechanical vibration and may generate the following effects: vibration, haptic, and the like. The electronic device 1001 may include a processing device (e.g., a GPU) for supporting a mobile TV. The processing device for supporting the mobile TV may process media data according to the standards of digital multimedia broadcasting (DMB), digital video broadcasting (DVB), MediaFLO™, or the like. Each of the above-mentioned elements of the electronic device according to various example embodiments of the present disclosure may be configured with one or more components, and the names of the elements may be changed according to the type of the electronic device. In various example embodiments, some elements of the electronic device (e.g., the electronic device 1001) may be omitted or other additional elements may be added. Furthermore, some of the elements of the electronic device may be combined with each other so as to form one entity, so that the functions of the elements may be performed in the same manner as before the combination.

Figure 11:
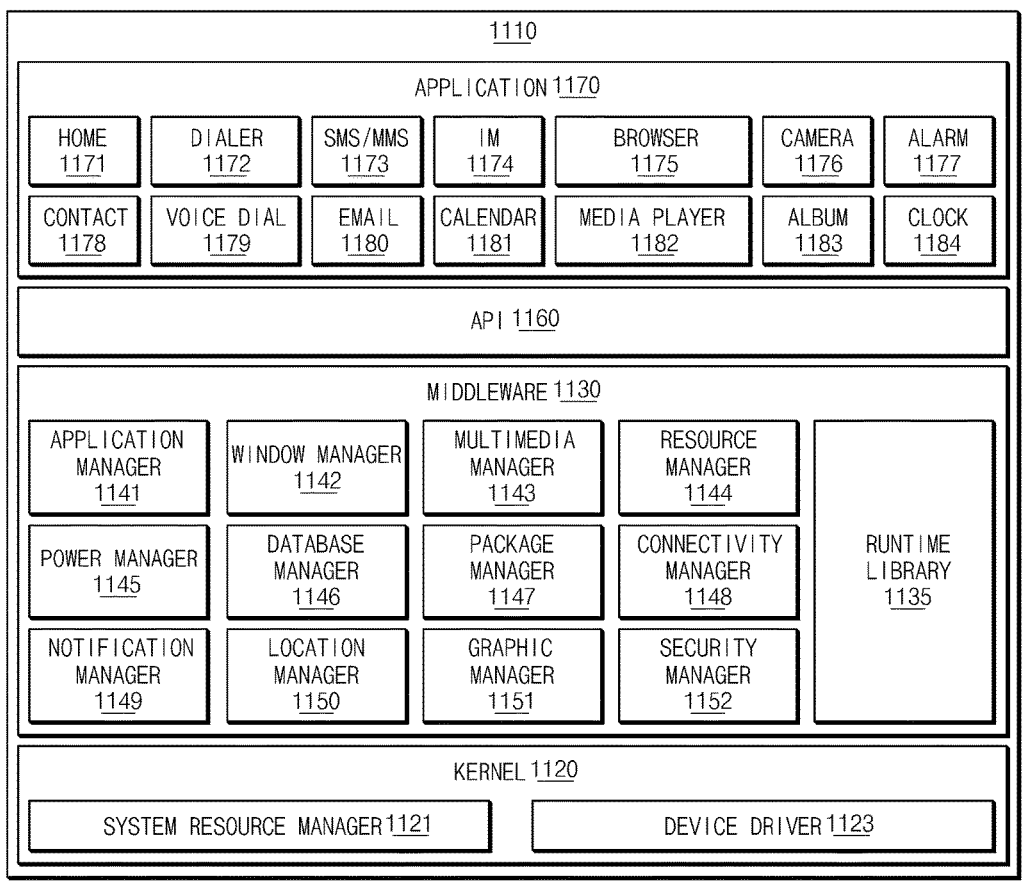
FIG. 11 is a block diagram of an example program module according to an example embodiment of the present disclosure.

FIG. 11 illustrates a block diagram of a program module, according to an example embodiment. According to an example embodiment, a program module 1110 (e.g., the program 940) may include an operating system (OS) to control resources associated with an electronic device (e.g., the electronic device 901), and/or diverse applications (e.g., the application program 947) driven on the OS. The OS may be, for example, Android™, iOS™, Windows™, Symbian™, Tizen™, or Bada™. The program module 1110 may include a kernel 1120 (e.g., the kernel 941), a middleware 1130 (e.g., the middleware 943), an application programming interface (API) 1160 (e.g., the API 945), and/or an application 1170 (e.g., the application program 947). At least a portion of the program module 1110 may be preloaded on an electronic device or may be downloadable from an external electronic device (e.g., the first electronic device 902, the second electronic device 904, the server 906, or the like).

The kernel 1120 (e.g., the kernel 941) may include, for example, a system resource manager 1121 or a device driver 1123. The system resource manager 1121 may control, allocate, or retrieve system resources. According to an example embodiment, the system resource manager 1121 may include a process managing unit, a memory managing unit, a file system managing unit, or the like. The device driver 1123 may include, for example, a display driver, a camera driver, a Bluetooth driver, a shared memory driver, a USB driver, a keypad driver, a Wi-Fi driver, an audio driver, or an inter-process communication (IPC) driver. The middleware 1130 may provide, for example, a function that the application 1170 needs in common, or may provide diverse functions to the application 1170 through the API 1160 to allow the application 1170 to efficiently use limited system resources of the electronic device. According to an example embodiment, the middleware 1130 may include, without limitation, at least one of a runtime library 1135, an application manager 1141, a window manager 1142, a multimedia manager 1143, a resource manager 1144, a power manager 1145, a database manager 1146, a package manager 1147, a connectivity manager 1148, a notification manager 1149, a location manager 1150, a graphic manager 1151, or a security manager 1152.

The runtime library 1135 may include, for example, a library module that is used by a compiler to add a new function through a programming language while the application 1170 is being executed. The runtime library 1135 may perform input/output management, memory management, or capacities about arithmetic functions. The application manager 1141 may manage, for example, a life cycle of at least one application of the application(s) 1170. The window manager 1142 may manage a graphic user interface (GUI) resource that is used in a screen. The multimedia manager 1143 may identify a format necessary for playing diverse media files, and may perform encoding or decoding of media files by using a codec suitable for the format. The resource manager 1144 may manage resources such as a memory space or source code of the application(s) 1170. The power manager 1145 may manage a battery or power, and may provide power information for an operation of an electronic device. According to an example embodiment, the power manager 1145 may operate with a basic input/output system (BIOS). The database manager 1146 may generate, search for, or modify database that is to be used in the application(s) 1170. The package manager 1147 may install or update an application that is distributed in the form of package file.

The connectivity manager 1148 may manage, for example, wireless connection. The notification manager 1149 may provide an event, for example, arrival message, appointment, or proximity notification to a user. For example, the location manager 1150 may manage location information about an electronic device. The graphic manager 1151 may manage a graphic effect that is provided to a user, or manage a user interface relevant thereto. The security manager 1152 may provide, for example, system security or user authentication. According to an example embodiment, the middleware 1130 may include a telephony manager for managing a voice or video call function of the electronic device or a middleware module that combines diverse functions of the above-described elements. According to an example embodiment, the middleware 1130 may provide a module specialized to each OS type to provide differentiated functions. Additionally, the middleware 1130 may dynamically remove a part of the preexisting elements or may add new elements thereto. The API 1160 may be, for example, a set of programming functions and may be provided with a configuration that is variable depending on an OS. For example, in a case in which an OS is Android or iOS, it may provide one API set per platform. In a case in which an OS is Tizen, it may provide two or more API sets per platform.

The application(s) 1170 may include, for example, applications such as a home 1171, a dialer 1172, an SMS/MMS 1173, an instant message (IM) 1174, a browser 1175, a camera 1176, an alarm 1177, a contact 1178, a voice dial 1179, an e-mail 1180, a calendar 1181, a media player 1182, an album 1183, a watch 1184, health care (e.g., measuring an exercise quantity, blood sugar, or the like) or offering of environment information (e.g., information of barometric pressure, humidity, temperature, or the like). According to an example embodiment, the application 1170 may include an information exchanging application to support information exchange between an electronic device and an external electronic device. The information exchanging application may include, for example, a notification relay application for transmitting specific information to an external electronic device, or a device management application for managing the external electronic device. For example, the notification relay application may include a function of transmitting notification information, which arise from other applications, to an external electronic device or may receive, for example, notification information from an external electronic device and provide the notification information to a user. The device management application may install, delete, or update for example, a function (e.g., turn-on/turn-off of an external electronic device itself (or a part of components) or adjustment of brightness (or resolution) of a display) of the external electronic device which communicates with the electronic device, and an application running in the external electronic device. According to an example embodiment, the application 1170 may include an application (e.g., a health care application of a mobile medical device) that is assigned in accordance with an attribute of an external electronic device. According to an example embodiment, the application 1170 may include an application that is received from an external electronic device. At least a portion of the program module 1110 may be implemented by software, firmware, hardware (e.g., the processor 1010), or a combination (e.g., execution) of two or more thereof, and may include modules, programs, routines, sets of instructions, processes, or the like for performing one or more functions.

The term "module" used in this disclosure may include a unit composed of hardware, software and firmware and may be interchangeably used with the terms "unit", "logic", "logical block", "component" and "circuit". The "module" may be an integrated component or may be a minimum unit for performing one or more functions or a part thereof. The "module" may be implemented mechanically or electronically and may include at least one of an application-specific IC (ASIC) chip, a field-programmable gate array (FPGA), and a programmable-logic device for performing some operations, which are known or will be developed. At least a part of an apparatus (e.g., modules or functions thereof) or a method (e.g., operations) according to various example embodiments may be, for example, implemented by instructions stored in computer-readable storage media (e.g., the memory 930) in the form of a program module. The instructions, when executed by a processor (e.g., the processor 920), may cause the processor to perform a function(s) corresponding to the instructions. A computer-readable recording medium may include a hard disk, a floppy disk, a magnetic media (e.g., a magnetic tape), an optical media (e.g., a compact disc read only memory (CD-ROM) and a digital versatile disc (DVD), a magneto-optical media (e.g., a floptical disk)), and an internal memory. Also, program instructions may include not only code such as things generated by a compiler, but also a high-level language code executable on a computer using an interpreter. A module or a program module according to various example embodiments may include at least one of the above elements, or a part of the above elements may be omitted, or other elements may be further included. Operations performed by a module, a program module, or other elements according to various example embodiments may be executed sequentially, in parallel, repeatedly, or in a heuristic method or some operations may be executed in different sequences or may be omitted. Alternatively, other operations may be added.

While the present disclosure has been shown and described with reference to various example embodiments thereof, it will be understood by those skilled in the art that various changes in form and details may be made therein without departing from the spirit and scope of the present disclosure as defined by the appended claims and their equivalents.

What is claimed is:

1. An electronic device comprising:
a display;
communication circuitry;
at least one sensor; and
a processor electrically connected with the display, the communication circuitry, and the at least one sensor,
wherein the processor is configured to:
based on first user-related state information obtained by the at least one sensor being determined to satisfy a predefined condition when a health state of a user corresponds to a first health state, control transmitting the first user-related state information to an external server through the communication circuitry;
control receiving, from the external server, through the communication circuitry, a first symptom check result corresponding to the first user-related state information;
set the health state of the user to a second health state different from the first health state based on the first symptom check result being determined to correspond to the second health state; and
control displaying a user interface (UI) for health management of the user at least once on the display until the health state of the user changes from the second health state to the first health state based on at least one of second user-related state information obtained subsequent to the first user-related state information by the at least one sensor being determined to not satisfy the predefined condition and a second symptom check result corresponding to the second user-related state information being determined to correspond to the first health state.

2. The electronic device of claim 1, wherein the at least one sensor includes one or more of an electromyography (EMG) sensor, an electroencephalogram (EEG) sensor, an electrocardiogram (ECG) sensor, an oxygen saturation measurement sensor, a gesture sensor, a gyro sensor, a barometric pressure sensor, a magnetic sensor, an acceleration sensor, a grip sensor, a proximity sensor, a temperature/humidity sensor, a photoplethysmograph (PPG) sensor, and a gas sensor.

3. The electronic device of claim 1, wherein the first user-related state information includes biometric information and user movement information.

4. The electronic device of claim 3, wherein the predefined condition is defined based on the biometric information and the user movement information.

5. The electronic device of claim 1, wherein the first health state corresponds to a normal health state, and the processor is configured to determine the normal health state of the user based on user-related state information obtained by the at least one sensor during a specified time period.

6. The electronic device of claim 1, wherein the processor is configured to control transmitting the first user-related state information to the external server based on context information obtained through the communication circuitry and the first user-related state information being determined to satisfy the predefined condition.

7. The electronic device of claim 1, wherein the second health state includes at least one of a self-care health state and a clinic health state.

8. The electronic device of claim 1, wherein the processor is configured to:
control displaying, on the display, a user interface (UI) for checking user symptoms;
control receiving user input to the UI; and
set the health state of the user based on at least one of the user input, the first user-related state information, and the first symptom check result.

9. The electronic device of claim 8, wherein the processor is configured to determine a type of the symptoms based on the first user-related state information.

10. The electronic device of claim 1, wherein the processor is configured to:
control displaying on the display of a UI to query whether to check user symptoms;
based on user input to the UI indicating not to check symptoms, control displaying a guide for user health management on the display.

11. The electronic device of claim 1, wherein the processor is configured to:
based on the second user-related state information being determined to not satisfy the predefined condition when the health state of the user is the second health state, control displaying on the display of a UI to query whether the user is recovered; and
set the health state of the user to the first health state based on a user input to the UI.

12. A user health management method for an electronic device, the method comprising:
obtaining first user-related state information;
based on the obtained first user-related state information being determined to satisfy a predefined condition when a health state of a user corresponds to a first health state, controlling transmitting of the first user-related state information to an external server;
controlling receiving from the external server of a first symptom check result corresponding to the first user-related state information;
setting the health state of the user to a health second state different from the first health state based on the first symptom check result being determined to correspond to the second health state; and
displaying a user interface (UI) for user health management at least once until the health state of the user changes from the second health state to the first health state based on at least one of second user-related state information obtained subsequent to the first user-related state information by the at least one sensor being determined to not satisfy the predetermined condition and a second symptom check result corresponding to the second user-related state information being determined to correspond to the first health state.

13. The method of claim 12, wherein the first user-related state information includes biometric information and user movement information.

14. The method of claim 12, further comprising:
before the transmitting of the first user-related state information, determining a normal health state of the user based on user-related state information obtained by at least one sensor during a specified period,
wherein the first health state corresponds to the normal health state.

15. The method of claim 12, further comprising:
obtaining context information of the user; and
controlling transmitting of the context information and the first user-related state information to the external server based on the context information and the first user-related state information being determined to satisfy the predefined condition.

16. The method of claim 12, further comprising:
displaying a UI to check user symptoms;
receiving a user input to the UI to check user symptoms; and
determining the health state of the user based on at least one of the first user-related state information and the user input to the UI to check user symptoms.

17. The method of claim 16, further comprising:
determining a type of symptoms to be checked based on the first user-related state information.

18. The method of claim 12, further comprising:
displaying a UI to query whether to check user symptoms;
based on a user input for not checking symptoms, controlling displaying of a guide for user health management.

19. The method of claim 12, further comprising:
based on the second user-related state information not satisfying the predefined condition when the health state of the user is the second health state, controlling displaying of a UI to query whether the user is recovered; and
setting the health state of the user to the first health state based on a user input to the recovery UI indicating user recovery.

20. A non-transitory computer-readable recording medium storing instructions that, when executed by an electronic device providing a function of managing a health state of a user, cause the electronic device to perform:
obtaining first user-related state information of the user;
based on the obtained first user-related state information being determined to satisfy a predefined condition when the health state of the user corresponds to a first health state, transmitting the first user-related state information to an external server;
receiving from the external server a first symptom check result corresponding to the first user-related state information;
setting a health state of the user to a second health state different from the first health state based on the first symptom check result being determined to correspond to the second health state; and
displaying a user interface (UI) for user health management at least once until the health state of the user changes from the second health state to the first health state based on at least one of second user-related state information obtained subsequent to the first user-related state information by the at least one sensor being determined to not satisfy the predetermined condition and a second symptom check result corresponding to the second user-related state information being determined to correspond to the first health state.

* * * * *